(12) United States Patent
Cevc et al.

(10) Patent No.: US 7,473,432 B2
(45) Date of Patent: Jan. 6, 2009

(54) NSAID FORMULATIONS, BASED ON HIGHLY ADAPTABLE AGGREGATES, FOR IMPROVED TRANSPORT THROUGH BARRIERS AND TOPICAL DRUG DELIVERY

(75) Inventors: Gregor Cevc, Gauting (DE); Ulrich Vierl, München (DE)

(73) Assignee: Idea AG, Munich (DE)

( * ) Notice: Subject to any disclaimer, the term of this patent is extended or adjusted under 35 U.S.C. 154(b) by 553 days.

(21) Appl. No.: 10/357,617

(22) Filed: Feb. 4, 2003

(65) Prior Publication Data
US 2004/0071767 A1 Apr. 15, 2004

Related U.S. Application Data

(60) Provisional application No. 60/417,847, filed on Oct. 11, 2002.

(51) Int. Cl.
*A61K 9/127* (2006.01)
(52) U.S. Cl. .................................. 424/450; 514/886
(58) Field of Classification Search .................. 424/450
See application file for complete search history.

(56) References Cited

U.S. PATENT DOCUMENTS 4,369,182 A  1/1983  Ghyczy et al.

(Continued)

FOREIGN PATENT DOCUMENTS

AU  1740283  7/1983

(Continued)

OTHER PUBLICATIONS

G. Ceve et al., Transdermal drug carriers: basic properties, optimization and transfer efficiency in the case of epicutaneously applied peptides, *J. Contr. Rel.*, 36, pp. 3-16, 1995.

(Continued)

*Primary Examiner*—Gollamudi Kishore
(74) *Attorney, Agent, or Firm*—Wilson Sonsini Goodrich & Rosati PC

(57) ABSTRACT

The invention describes novel formulations of nonsteroidal anti-inflammatory drugs (NSAIDs) based on complex aggregates with at least three amphipatic components suspended in a suitable, e.g. pharmaceutically acceptable, polar liquid medium. A suitably ionised NSAID is one of the two, amongst said three, components that tends to destabilise lipid membranes, the other system component with such activity being typically a surfactant. In contrast, the remaining amongst said at least three amphipatic components typically forms a stable lipid membrane on it's own. An essential characteristics of the resulting, relatively large, aggregates is an improved ability to penetrate pores, in a semi-permeable barrier, at least 30%, and often much smaller than the average diameter of the complex aggregate. This enables said aggregates to mediate NSAID transport through semi-permeable barriers including mammalian skin. As a result of the skin penetration by NSAID loaded large aggregates, the drug delivered transcutaneously with such carriers gets deeper into the tissue than the corresponding NSAID from a solution on the skin surface. This is believed to be due to the special ability of suitable large carriers to bypass the local sink of blood capillaries at the epidermal-dermal junction in the skin. The carrier-mediated delivery of locally applied NSAIDs thus allows therapy of deep tissues under the drug administration site, which is medically highly desirable.

80 Claims, 3 Drawing Sheets

U.S. PATENT DOCUMENTS

| | | | |
|---|---|---|---|
| 4,619,794 A | 10/1986 | Hauser | |
| 4,666,747 A | 5/1987 | Quinn | |
| 4,731,210 A | 3/1988 | Weder et al. | |
| 4,746,509 A | 5/1988 | Haggiage et al. | |
| 4,783,450 A | 11/1988 | Fawzi et al. | |
| 4,849,224 A | 7/1989 | Chang et al. | |
| 4,897,269 A | 1/1990 | Mezei | |
| 4,911,928 A | 3/1990 | Wallach | |
| 4,921,706 A | 5/1990 | Roberts et al. | |
| 4,937,078 A | 6/1990 | Mezei et al. | |
| 4,937,182 A | 6/1990 | Hancock et al. | |
| 4,937,254 A | 6/1990 | Sheffield et al. | |
| RE33,273 E | 7/1990 | Speaker | 210/639 |
| 4,944,948 A | 7/1990 | Uster et al. | 424/450 |
| 4,954,345 A | 9/1990 | Miller | |
| 4,983,395 A | 1/1991 | Chang et al. | |
| 5,043,165 A | 8/1991 | Radhakrishnan | |
| 5,104,661 A | 4/1992 | Lau | |
| 5,145,684 A | 9/1992 | Liversidge et al. | |
| 5,154,930 A | 10/1992 | Popescu et al. | |
| 5,202,125 A | 4/1993 | Ebert et al. | |
| 5,209,720 A | 5/1993 | Unger | |
| 5,238,613 A | 8/1993 | Anderson | 264/22 |
| 5,244,678 A | 9/1993 | Legros et al. | |
| 5,322,685 A | 6/1994 | Nakagawa et al. | 424/78.03 |
| 5,460,820 A | 10/1995 | Ebert et al. | |
| 5,498,418 A | 3/1996 | Beutner et al. | |
| 5,498,420 A | 3/1996 | Edgar et al. | |
| 5,510,118 A | 4/1996 | Boasch et al. | |
| 5,552,160 A | 9/1996 | Liversidge et al. | |
| 5,585,109 A | 12/1996 | Hayward et al. | |
| 5,607,692 A | 3/1997 | Ribier et al. | 424/450 |
| 5,614,178 A | 3/1997 | Bloom et al. | |
| 5,648,095 A | 7/1997 | Illum et al. | |
| 5,654,337 A | 8/1997 | Roentsch et al. | |
| 5,681,849 A | 10/1997 | Richter et al. | |
| 5,716,638 A | 2/1998 | Touitou | |
| 5,741,515 A | 4/1998 | Ciceri et al. | |
| 5,763,422 A | 6/1998 | Lichtenberger et al. | |
| 5,783,208 A | 7/1998 | Venkateshwaran et al. | |
| 5,837,289 A | 11/1998 | Grasela et al. | |
| 5,858,330 A | 1/1999 | Boltri et al. | |
| 5,874,095 A | 2/1999 | Deckner et al. | |
| 5,874,422 A | 2/1999 | Krause et al. | |
| 5,891,472 A | 4/1999 | Russell | |
| 5,958,379 A | 9/1999 | Regenold et al. | 424/47 |
| 5,985,860 A | 11/1999 | Toppo | |
| 6,028,066 A | 2/2000 | Unger | |
| 6,045,827 A | 4/2000 | Russell | |
| 6,069,172 A | 5/2000 | Bertini et al. | |
| 6,083,996 A | 7/2000 | Buyuktimkin et al. | |
| 6,165,500 A * | 12/2000 | Cevc | 424/450 |
| 6,193,996 B1 | 2/2001 | Effing et al. | |
| 6,200,598 B1 * | 3/2001 | Needham | 424/450 |
| 6,214,386 B1 | 4/2001 | Santus et al. | |
| 6,248,353 B1 | 6/2001 | Singh | |
| 6,277,892 B1 | 8/2001 | Deckner et al. | |
| 6,294,192 B1 | 9/2001 | Patel et al. | |
| 6,303,141 B1 | 10/2001 | Fischer et al. | |
| 6,387,383 B1 | 5/2002 | Dow et al. | |
| 6,448,296 B2 | 9/2002 | Yasueda et al. | |
| 6,451,339 B2 | 9/2002 | Patel et al. | |
| 6,562,370 B2 | 5/2003 | Luo et al. | |
| 6,577,880 B1 | 6/2003 | Ishida et al. | |
| 6,582,724 B2 | 6/2003 | Hsu et al. | |
| 6,586,000 B2 | 7/2003 | Luo et al. | |
| 6,645,520 B2 | 11/2003 | Hsu et al. | |
| 6,645,529 B2 | 11/2003 | Gergely et al. | |
| 6,654,337 B2 | 11/2003 | Endoh et al. | |
| 6,726,598 B1 * | 4/2004 | Jarvis et al. | 482/13 |
| 6,726,925 B1 | 4/2004 | Needham | |
| 6,797,276 B1 | 9/2004 | Glenn et al. | |
| 6,835,392 B2 | 12/2004 | Hsu et al. | |
| 6,868,686 B2 | 3/2005 | Ueda et al. | |
| 7,175,850 B2 | 2/2007 | Cevc | |
| 2001/0012849 A1 | 8/2001 | Wechter | |
| 2002/0003179 A1 | 1/2002 | Verhoff et al. | |
| 2002/0012680 A1 | 1/2002 | Patel et al. | |
| 2002/0037877 A1 | 3/2002 | Singh | |
| 2002/0048596 A1 | 4/2002 | Cevc | |
| 2002/0106345 A1 | 8/2002 | Uhrich et al. | |
| 2002/0119188 A1 | 8/2002 | Niemiec et al. | |
| 2002/0147238 A1 | 10/2002 | Jerussi et al. | |
| 2003/0099694 A1 | 5/2003 | Cevc et al. | |
| 2004/0071767 A1 | 4/2004 | Cevc et al. | |
| 2004/0105881 A1 | 6/2004 | Cevc | |
| 2005/0123897 A1 | 6/2005 | Cevc et al. | |
| 2007/0031483 A1 | 2/2007 | Cevc | |
| 2007/0042030 A1 | 2/2007 | Cevc | |
| 2007/0184114 A1 | 8/2007 | Cevc | |
| 2007/0243203 A1 | 10/2007 | Abrecht et al. | |

FOREIGN PATENT DOCUMENTS

| | | |
|---|---|---|
| AU | 724218 | 5/1998 |
| CA | 1 143 656 | 3/1983 |
| CA | 1143656 | 3/1983 |
| CA | 1289420 | 9/1991 |
| CA | 2 067 754 | 3/1992 |
| CA | 2052164 | 9/1992 |
| CA | 2160775 | 11/1994 |
| DE | 3016976 | 11/1980 |
| DE | 3713494 | 10/1987 |
| DE | P 40 26 833.0-43 | 2/1992 |
| DE | P 40 26 834.9-41 | 2/1992 |
| DE | 4107152 | 9/1992 |
| DE | 4107153 | 9/1992 |
| DE | 4447287 | 11/1996 |
| EP | 0 102 324 | 7/1983 |
| EP | 0102324 | 3/1984 |
| EP | 0 152 379 A2 | 2/1985 |
| EP | 0152376 | 8/1985 |
| EP | 0224837 | 11/1986 |
| EP | 0211647 | 2/1987 |
| EP | 0 220 797 * | 5/1987 |
| EP | 0220797 | 5/1987 |
| EP | 0 088 046 B1 | 12/1987 |
| EP | 0 298 280 | 6/1988 |
| EP | 0280492 | 8/1988 |
| EP | 0 393 707 | 4/1990 |
| EP | 0475160 | 3/1992 |
| EP | 0 355 095 | 8/1993 |
| EP | 0582239 | 3/1994 |
| EP | 0674913 | 10/1995 |
| EP | 0704206 | 4/1996 |
| EP | 0707847 | 4/1996 |
| EP | 0 382 716 | 1/1998 |
| EP | 0 995 435 | 4/2000 |
| EP | 1 031 347 | 4/2002 |
| EP | 1 031 346 B1 | 5/2002 |
| EP | 0475160 B2 | 7/2004 |
| EP | 1140021 B1 | 8/2004 |
| HU | 9903363 | 3/2000 |
| HU | 0104424 | 3/2002 |
| HU | 0105400 | 5/2002 |
| JP | 61-271204 | 12/1986 |
| JP | 07-324029 | 12/1995 |
| JP | 2006131597 | 5/2006 |
| WO | WO 87/01938 | 4/1987 |
| WO | WO 88/07362 | 10/1988 |
| WO | WO-90/09385 | 8/1990 |
| WO | WO 90/09782 | 9/1990 |
| WO | WO 90/11065 | 10/1990 |
| WO | WO-91/01146 | 2/1991 |

| | | |
|---|---|---|
| WO | WO 91/04013 | 4/1991 |
| WO | WO 92/03122 | 3/1992 |
| WO | WO-92/04009 | 3/1992 |
| WO | WO 92/05771 | 4/1992 |
| WO | WO 93/19736 | 10/1993 |
| WO | WO 93/19737 | 10/1993 |
| WO | WO-94/26257 | 11/1994 |
| WO | WO-95/35095 | 12/1995 |
| WO | WO 96/19205 | 6/1996 |
| WO | WO-96/29999 | 10/1996 |
| WO | WO-92/22292 | 2/1998 |
| WO | WO 98/06750 | 2/1998 |
| WO | WO-98/07414 | 2/1998 |
| WO | WO 98/17255 | 4/1998 |
| WO | WO-98/24407 | 6/1998 |
| WO | WO 98/30215 | 7/1998 |
| WO | WO 98/33483 | 8/1998 |
| WO | WO-99/22703 | 5/1999 |
| WO | WO 00/00597 | 1/2000 |
| WO | WO 00/12060 | 3/2000 |
| WO | WO-00/13684 | 3/2000 |
| WO | WO 00/24377 | 5/2000 |
| WO | WO-00/25822 | 5/2000 |
| WO | WO-00/38653 | 7/2000 |
| WO | WO 00/38653 | 7/2000 |
| WO | WO-00/44349 | 8/2000 |
| WO | WO-00/44350 | 8/2000 |
| WO | WO 00/44350 | 8/2000 |
| WO | WO-00/50007 | 8/2000 |
| WO | WO-01/00247 | 1/2001 |
| WO | WO 01/01962 | 1/2001 |
| WO | WO-01/01963 | 1/2001 |
| WO | WO-01/12155 | 2/2001 |
| WO | WO-02/07767 A2 | 1/2002 |
| WO | WO-02/11683 | 2/2002 |
| WO | WO-02/32398 | 4/2002 |
| WO | WO-02/058670 | 8/2002 |
| WO | WO-2004/032900 | 4/2004 |
| WO | WO-2005/063213 | 7/2005 |
| WO | WO-2006/050926 | 5/2006 |

OTHER PUBLICATIONS

S. Yuan, et al., Cationic Liposome and Gene Transfer, *Progress in Physiological Science*, 28(2), pp. 163-165, 1997.

G. Cevc, Transfersomes, Liposomes and Other Lipid Suspensions on the Skin: Permeation Enhancement, Vesicle Penetration, and Transdermal Drug Delivery,*Crit. Rev. Ther. Drug Carrier Syst.*, 13(3 &4), pp. 257-388, 1996.

A. Klibanov, et al., Activity of amphiphatic poly(ethylene glycol) 5000 to prolong the circulation time of liposomes depends on the liposome size and is unfavorable for immunoliposome binding to target, *BBA*, 1062, pp. 141-148, 1991.

Benner, "The Human Body, The Wonderwork of the Human Body, Structure, Functions, Interactions, Processes and Mechanisms" Weltbild GmbH Augsburg (1995).

Serva, Feinbiochemica fur Forshung for *Serva Feinbiochemica GmbH & Co.* (1986/1987).

Clark, J.M., Jr., "Experimental Biochemistry" Biochemistry Division, Department of Chemistry, University of Illinois, pp. 47-48.

Patel, H.M. "Liposomes as a Controlled-release System" Biomedical Society Transactions 609th Meeting, Leeds, pp. 513-516.

Fieser, L.F., et al. "Organische Chemie" *Hans Ruprecht Hensel, 2nd revised edition, Verlag Chemie GmbH, Weinheim/Bergstr* (1968).

Fluka Chemika-BioChemika Catalogue 16 (1988/89).

Roeding, J., "Liposomes and Niosomes in Pharmacy and Cosmetic State of the Art Prospects, Techniques of Visualizing Vesicular Systems, Interaction of Liposomes with the Skin" *Training Course No. 105 from May 14 to 16, 1990, MARITIM Hotel Nurnberg, Frauentorgraben 11, 8500 Nurenbwerg*.

Office Action mailed Apr. 2, 2008 in connection with U.S. Appl. No. 09/284,683, assigned to IDEA AG.

Claims pending on Apr. 2, 2008 in connection with U.S. Appl. No. 09/284,683, assigned to IDEA AG.

Office Action mailed Aug. 10, 2006 in connection with U.S. Appl. No. 09/555,986, assigned to IDEA AG, now abandoned.

Claims pending on Aug. 10, 2006 in connection with U.S. Appl. No. 09/555,986, assigned to IDEA AG, now abandoned.

Office Action mailed Jan. 9, 2008 in connection with U.S. Appl. No. 10/037,480, assigned to IDEA AG.

Claims pending on Jan. 9, 2008 in connection with U.S. Appl. No. 10/037,480, assigned to IDEA AG.

Office Action mailed May 15, 2008 in connection with U.S. Appl. No. 10/984,450, assigned to IDEA AG.

Claims pending on May 15, 2008 in connection with U.S. Appl. No. 10/984,450, assigned to IDEA AG.

Office Action mailed Mar. 19, 2008 in connection with U.S. Appl. No. 10/357,618, assigned to IDEA AG.

Claims pending on Mar. 19, 2008 in connection with U.S. Appl. No. 10/357,618, assigned to IDEA AG.

Almeida et al., "Nasal delivery of vaccines," Journal of Drug Targeting, vol. 3, No. 6, pp. 455-467 (1996).

Byas-Smith et al., "Transdermal clonidine compared to placebo in painful diabetic neuropathy using two stage 'enriched enrollment' design," Pain, vol. 60, pp. 267-274 (1995).

Castillo et al., "Glucocorticoids Prolong Rat Sciatic Nerve Blockade In Vivo from Bupivacaine Microspheres," Anesthesiology, vol. 85, No. 5, pp. 1157-1166 (1996).

Cevc et al., "Phospholids handbook", Marcel Dekker, Inc., New York, Basel, Hong Kong, pp. 375-376 and 404 (1993).

Claims presently pending in U.S. Appl. No. 09/890,335.

Claims presently pending in U.S. Appl. No. 09/890,371.

Claims filed Jan. 22, 2007, in connection with U.S. Appl. No. 10/037,480 (U.S. Patent Publication No. US 2003/0099694 A1).

Claims filed Mar. 20, 2006, in connection with U.S. Appl. No. 10/037,480 (U.S. Patent publication No. US 2003/0099694 A1).

Claims filed Sep. 21, 2005, in connection with U.S. Appl. No. 10/037,480 (U.S. Patent Publication No. US 2003/0099694 A1).

Claims filed Oct. 20, 2004, in connection with U.S. Appl. No. 10/037,480 (U.S. patent Publication No. US 2003/0099694 A1).

Claims filed Jan. 4, 2002, in connection with U.S. Appl. No. 10/037,480 (U.S. Patent Publication No. US 2003/0099694 A1).

Claims filed Feb. 26, 2007, in connection with U.S. Appl. No. 10/984,450 (U.S. Patent Publication No. US 2005/0123897 a1).

Claims filed May 31, 2005, in connection with U.S. Appl. No. 10/984,450 (U.S. Patent Publication No. US 2005/0123897 A1).

Claims filed May 31, 2006, in connection with U.S. Appl. No. 10/984,450 (U.S. Patent Publication No. US 2005/0123897 A1).

Claims filed May 12, 2004, in connection with U.S. Patent Application No. 10/357,618 (U.S. Patent Publication No. 2004/0105881 A1).

International Search Report for International Patent Application No. PCT/EP2005/011986. (Jul. 4, 2006).

Definition of Microbicide, Wikipedia, The Free Online encyclopedia (2007).

Frantzen et al., "Assessing the accuracy of routine Photon Correlation Spectroscopy Analysis of Heterogeneous Size Distributions," AAPS PharmSciTech, vol. 4, No. 3, Article 36, pp. 1-9 (2003).

Glen et al, "Skin immunization made possible by cholera toxin letter!", Nature, GB, MacMillan Journal LTD., London, vol. 391, No. 6670, pp. 851 (Feb. 1998).

Grahame R, "Transdermal non-steroidal anti-inflammatory agents," BJCP, vol. 49, No. 1, pp. 33-35 (Jan.-Feb. 1995).

Holzbach RT, "Detection of Vesicles in native and model Biles by Morphological and other structural Techniques: applications and limitations," Hepatology, Sep. 12 (3 Pt 2), pp. 106S-112S (1990).

Lehmann, J. et al. "Analgesic and anti-inflammatory efficacy of IDEA-070 in UVB-induced sunburn." Journal of the European Academy of Dermatology and Venereology, 18(S2):167-168. (Oct. 2004).

Merck Index: 10th Edition. pp. 779-780. (1983).

Office Action issued Apr. 11, 2007, in connection with U.S. Appl. No. 10/037,480 (U.S. Patent Publication No. US 2003/0099694 A1).

Office Action issued Sep. 20, 2006, in connection with U.S. Appl. No. 10/037,480 (U.S. Patent Publication No. US 2003/0099694 A1).

Office Action issued Dec. 19, 2005, in connection with U.S. Appl. No. 10/037,480 (U.S. Patent Publication No. US 2003/0099694 A1).

Office Action issued Mar. 30, 2005, in connection with the U.S. Appl. No. 10/037,480 (U.S. Patent Publication No. U.S. 2003/0099694 A1).
Office Action issued on Oct. 16, 2003, in connection with U.S. Appl. No. 10/037,480 (U.S. Patent Publication No. US 2003/0099694 A1).
Office Action issued on May 16, 2007, in connection with U.S. Appl. No. 10/984,450 (U.S. Patent Publication No. 2005/0123897 A1).
Office Action issued on Feb. 7, 2006, in connection with U.S. Appl. No. 10/984,450 (U.S. Patent Publication No. US 2005/0123897 A1).
Office Action issued on Aug. 28, 2006, in connection with U.S. Appl. No. 10/984,450 (U.S. Patent Publication No. US 2005/0123897 A1).
Office Action issued Dec. 28, 2006, in connection with U.S. Appl. No. 10/357,618 (U.S. Patent Publication No. 2004/0105881 A1).
Paul et al., "Non Invasive administration of protein antigens: transdermal immunization with bovine serum albumin in transfersomes," Vaccine Research, vol. 4, No. 3, pp. 145-164 (1995).
Paul et al., "Transdermal immunisation with an integral membrane component, gap junction protein, by means of ultradeformable drug carriers, transfersomes," Vaccine, vol. 16, No. 2-3, pp. 188-195 (Jan. 1998).
Product Information, "Polysorbate 80 VG" (2004).
Product Information, "Tween 80 Pure" (2004).
Ranade V., "Drug Delivery Systems.6. Transdermal Drug Delivery," J. Clin Pharmacol, vol. 31, pp. 401-418 (1991).
Swenson, E. Scott and William J. Curatolo. "Intestinal permeability enhancement for proteins, peptides and other polar drugs: mechanisms and potential toxicity." Advanced Drug Delivery Reviews, 8:39-92. (1992).
Trotta, M. et al. "Deformable liposomes for dermal administration of methotrexate." International Journal of Pharmaceutics, 270:119-125. (Feb. 11, 2004).
Trotta, M. et al. "Elastic liposomes for skin delivery of dipotassium glycyrrhizinate." International Journal of Pharmaceutics, 241(2):319-327. (Jul. 25, 2002).
Wess, L. "Down, down, deeper and down." Biocentury, The Bernstein Report on BioBusiness, 12(22):A11-A12. (May 17, 2004).
Erjavec, et al. "In vivo study of liposomes as drug carriers to oral mucosa using EPR oximetry." Int. J. Pharmaceut. 307: 1-8. (2006).
English Abstract of Anosov, et al. "Electrical capacitance of hydrogenated egg lecithin bilayer lipid membranes in the lipid crystal to gel phase transition." Biofizika. 48(2): 240-245. (2003).
G. Cevc et al., Transfersomes-mediated transepidermal delivery improves the regio-specificity and biological actibity of corticosteroids in vivo, *Journal of Controlled Release* 45 (1997) 211-226.
V.M. Knepp et al. Controlled Drug Release From a Novel Liposomal Delivery System II. Transdermal Delivery Characteristics, Journal of Controlled Release 12 (Mar. 1990), No. 1, Amsterdam, NL, pp. 25-30.
C.E. Price, "A Review of the Factors Influencing the Penetration of Pesticides Through Plant Leaves" on I.C.I. Ltd., Plant Protection Division, Jealott's Hill Research Station, Bracknell, Berkshire RG12 6EY, U.K., pp. 237-252.
K. Karzel and R. K. Liedtke, "Mechanismen Transkutaner Resorption" on Grandlagen/Basics, pp. 1487-1491.
Michael Mezei, "Liposomes as a Skin Drug Delivery System" 1985 Elsevier Science Publishers B.V. (Biomedical Division), pp. 345-358.
Adrienn Gesztes and Michael Mezei, "Topical Anesthesia of the Skin by Liposome-Encapsulated Tetracaine" on Anesth Analg 1988; 67: pp. 1079-1081.
A. Helenius, et al, "Solubilization of Membranes by Detergents", Biochimica et Biophysica Acta, 415 (1975) 29-79.
Phillip G. Green, et al., "In Vitro and In Vivo Enhancement of Skin Permeation With Oleic and Lauric Acids" on International Journal of Pharmaceutics, 48 (1988), pp. 103-111.
Guia M. Golden et al. "Role of Stratum Corneum Lipid Fluidity in Transdermal Drug Flux" on Journal of Pharmaceutical Sciences vol. 76, No. 1, Jan. 1987, American Pharmaceutical Association, pp. 25-28.
Bruce J. Aungst et al., "Enhancement of Naloxone Penetration Through Human Skin In Vitro Using Fatty Acids, Fatty Alcohols, Surfactants, Sulfoxides and Amides" on International Journal of Pharmaceutics, 33 (1986) pp. 225-234.
Ronald R. Burnette et al., "Characterization of the Permselective Properties of Excised Human Skin During Lontophoresis" on Journal of Pharmaceutical Sciences vol. 76, No. 10, Oct. 1987, American Pharmaceutical Association, pp. 765-773.
E.C. Katoulis et al., "Efficacy of a New Needeless Insulin Delivery System Monitoring of Blood Glucose Fluctuations and Free Insulin Levels" on International Journal of Artificial Organs vol. 12, No. 5, 1989, pp. 333-338.
Ovals Siddiqui et al., "Nonparenteral Administration of Peptide and Protein Drugs" on CRC Critical Reviews in Therapeutic Drug Carrier Systems, vol. 3, Issue 3, pp. 195-208.
Cevc, G. et al., "Ultraflexible vesicles, Transfersomes, have an extremely low pore penetration resistance and transport therapeutic amounts of insulin across the intact mammalian skin", Biochimica et Biophysica Acta. 1368 pp. 201-215 (1998).
Cevc, G. "Material Transport Across Permeability Barriers by Means of Lipid Vesicles", Handbook of Biological Physics, vol. 1, pp. 465-490 (1995).
Mayer, L.D. et al., "Vesicles of variables sizes produced by a rapid extrusion procedure", Biochimica et Biophysica Acta, 858 pp. 161-165 (1986).
Patel, H.M. et al., "Oral Administration of Insulin by Encapsulation Within Liposomes", FEBS Letters, 62(1):60-63 (Feb. 1976).
Schreier, H. "Liposomes—A Novel Drug Carrier, I. Phospholipids; Production and Characterization of Liposomes; II. Destiny of liposomes in vivo; use in therapy", Pharmazie in unserer Zeit, No. 4 (1982).
Beyer, C. et al., "Micro Emulsions" Pharmazie in unserer Zeit, No. 2 (1983).
Lichtenberg, D. et al., "Solubilization of Phospholipids by Detergents Structural and Kinetic Aspects" Biochimica et Biophysica Acta, 737 pp. 285-304 (1983).
Lasch, J. et al., "Interactions of external lipids (lipids vesicles) with the skin" Journal of Liposome Research 5(3) pp. 543-569 (1995).
Berger, M. "Oral Insulin 1922-1992: The History of Continuous Ambition and Failure" Heinrich-Heine-University, Dusseldorf, Germany.
Cevc. G. et al., "The skin: a pathway for systemic treatment with patches and lipid-based agent carriers" Advanced Drug Delivery Reviews 18 pp. 349-378 (1996).
M.L. Jackson, et al. "Solubilization of Phosphatidylcholine Bilayers by Octyl Glucoside", biochemistry 1982, 21, 4576-4582.
P. Vinson, et al. "Vesicle-Micelle Transition of Phosphatidylcholine and Octyl Glucoside Elucidated by Cryo-Transmission Ele Tron Microscopy", Biophys. J., Biophysical Society vol. 56 Oct. 1989 669-681.
K. Edwards, et al. "Effects of Triton X-100 on Sonicated Lecithin Vesicles", Langmuir, vol. 5, No. 2, 1989 pp. 473-478.
A. Brendzel, et al., "Effects of Lipid-Soluble Substances on the Thermotropic Properties of Liposome Filtration", Biochimica et Biophysica Acta, 601 (1980) 260-270.
G. Blume, et al. "Drug-Carrier and Stability Properties of the Long-Lived Lipid Vesicles, Cryptosomes, In Vitro and In Vivo", Journal of Liposome Research, 2(3), 355-368 (1992).
L. Löbbecke, et al. "Effects Of Short-Chain Alcohols On The Phase Behavior And Interdigitation Of Phosphatidylcholine Bilayer Membranes", Biochimiea et Biophysica Aeta 1237 (1995) 59-69.
R. Singh, et al. "Liposomally Encapsulated Diclofenac For Sonophoresis Induced Systemic Delivery", J. Microencapsulation, 1995, vol. 12, No. 2, 149-154.
G. Cevc, et al. "Newly, Highly Efficient Formulation of Diclofenac For the Topical, Transdermal Administration In Ultradeformable Drug Carriers, Transfersomes", Biochimica et Biophysica Acta 1514 (2001) 191-205.
A. Calpena, et al., "Influence of the Formulation on the In Vitro Transdermal Penetration of Sodium Diclofenac", Arzneim.-Forsch./Drug Res. 49 (II), 1012-1017 (1999).
I. Friedrich, et al., "Physicochemical Characterization of a Reverse Micellar Solution after Loading with Different Drugs", Pharmazie 55 (2000) 10, 755-758.

I. Stoye, et al., "Transformation of a Liposomal Dispersion Containing Ibuprofen Lysinate and Phospholipids into Mixed Micelles—Physico-chemical Characterization and Influence on Drug Permeation through Excised Human Stratum Corneum," European Journal of Pharmaceutics and Biopharmaceutics 46 (1998) 191-200.

C. Valenta, et al., "Evaluation of Novel Soya-lecithin Formulations for Dermal use containing Ketoprofen as a Model Drug", Journal of Controlled Release 63 (2000) 165-173.

T. Henmi, et al., "Application of an Oily Gel Formed by Hydrogenated Soybean Phgospholipids as a Percutaneous Absorption-Type Ointment Base", Chem. Pharm. Bull. 42(3) 651-655 (1994).

J. Schramlova, et al., "The Effect of an Antiphlogistic Incorporated in Liposomes on Experimentally Induced Inflammation", Folia Biologica (Praha) 43, 195-199 (1997).

A. Gesztes, et al., "Topical Anesthesia of the Skin by Liposome-Encasulated Tetracaine", Anesth Analg 1988 67 1079-1081.

M. Foldvari, et al., "Dermal Drug Delivery by Liposome Encapsulation: Clinical and Electron Microscopic Studies", J. Microencapsulation, 1990, vol. 7, No. 4, 479-489.

M. Foldvari, "In Vitro cutaneous and Percutaneous Delivery and in Vivo Efficacy of Tetracaine from Liposomal and Conventional Vehicles", Pharmaceutical Research, vol. 11, No. 11, 1994.

M. Foldvari, "Effect of Vehicle on Topical Liposomal Drug Delivery: Petrolatum Bases", J. Microencapsulation, 1996, vol. 13, No. 5, 589-600.

M.E. Planas, et al., "Noninvasive Percutaneous Induction of Topical Analgesia by a New Type of Drug Carrier, and Prolongation of Local Pain Insensitivity by Anesthetic Liposomes", Anesth Analg 1992; 75 615-621.

H. Peters, et al., "Pharmacodynamics of a Liposomal Preparation for Local Anaesthesia", Arzneim.-Forsch./Drug Res. 45 (II), Nr 12 (1995).

M. Carafa, et al., "Lidocaine-loaded Non-ionic Surfactant Vesicles: Characterization and In Vitro Permeation Studies", International Journal of Pharmaceutics 231 (2002) 21-32.

G. Cevc, "Drug Delivery Across the Skin", Exp. Opin. Invest. Drugs (1997) 6(12) 1887-1937.

C.E. Price, "A Review of the Factors Influencing the Penetration of Pesticides through Plant Leaves", Linnean Society Symposium Series, No. 10 pp. 237-252.

O. Siddiqui, et al., "Nonparenteral Administration of Peptide and Protein Drugs", CRC Critical Reviews in Therapeutic Drug Carrier Systems, vol. 3, Issue 3 p. 195-208.

R. Burnette, et al., "Characterization of the Permselective Properties of Excised Human Skin During Lontophoresis", Journal of Pharmaceutical Sciences/ vol. 76, No. 10. Oct. 1987 pp. 765-773.

Price, C.E. "A review of the factors influencing the penetration of pesticides through plant leaves." In *The plant cuticle*, D. F. Cutler, K. L. Alvin and C. E. Price, Editors. New York, Academic Press, 1982, p. 237-252.

Prof. Dr. K-U Benner, *Der Korper des Menschen*, Chapter 4, p. 49 (1995).

http://www.serva.de/products/data/33116.01.shtml Polysorbate 80 VG (2004).

http://www.serva.de/products/data/37475.01.shtml Tween® 80 pure (2004).

*Merck Index*: 10th Edition. 1983, pp. 779-780.

Burnham et al., "The effectiveness of topical diclofenac for lateral epicondylitis", Clin J Sport Med 8(2):78-81, 1998.

Cevc et al., "Ultradeformable lipid vesicles can penetrate the skin and other semi-permeable barriers unfragmented. Evidence from double label CLSM experiments and direct size measurements", Biochimica et Biophysica Acta 1564:21-30, 2002.

Frisken et al., "Studies of vesicle extrusion", Langmuir 16:928-933, 2000.

Hunter and Frisken, "Effect of extrusion pressure and lipid properties on the size and polydispersity of lipid vesicles", Biophys J 74:2996-3002, 1998.

Ito et al., "Percutaneous absorption of acemetacin from a membrane controlled transdermal system and prediction of the disposition of the drug in rats", Biol Pharm Bull 16(6):583-8, 1993.

Ogiso et al., "Membrane-controlled transdermal therapeutic system containing clonazepam and anticonvulsant activity after its application", Chem Pharm Bull 37(2):446-449, 1989.

Saunders et al., "A novel skin penetration enhancer: evaluation by membrane diffusion and confocal microscopy", J Pharm Pharmaceut Sci 2(3):99-107, 1999.

Pending claims in connection with U.S. Appl. No. 09/284,683.
Pending claims in connection with U.S. Appl. No. 10/555,986.
Pending claims in connection with U.S. Appl. No. 10/037,480.
Pending claims in connection with U.S. Appl. No. 10/984,450.
Pending claims in connection with U.S. Appl. No. 10/357,618.
Pending claims in connection with U.S. Appl. No. 11/545,904.

Attachment filed by Opponent Nov. 14, 1996 in connection with EP 0475160B1 Opposition (in German).

Patentee's response to Opposition Request filed Apr. 21, 1997 in connection with EP 0475160B1 (in German).

Patentee communication to the EPO filed May 22, 1998 in connection with EP 0475160B1 Opposition (in German).

Opponent's response filed May 22, 1998 in connection with EP 0475160B1 Opposition (in German).

Decision of EP Opposition Division Jul. 30, 1998 in connection with EP 0475160B1 Opposition (in German).

Appeal by Opponent in connection with EP 0475160B1 Opposition (in German).

Response by Patentee filed Apr. 19, 1999 in connection with EP 0475160B1 Opposition (in German).

English translation of Opposition filed Feb. 6, 1997 in connection with DE 4447287 C1 Opposition.

English translation of counterstatement of Patentee filed Jul. 11, 1997 in connection with DE 4447287 C1 Opposition.

English translation of Opponent's response to Office Action filed Mar. 17, 1998 in connection with DE 4447287 C1 Opposition.

English translation of Patentee's response to Office Action filed Feb. 9, 1999 in connection with DE 4447287 C1 Opposition.

U.S. Appl. No. 11/929,544, entitled "Method for developing, testing and using associates of macromolecules and complex aggregates for improved payload and controllable de/association rates", filed Oct. 30, 2007.

U.S. Appl. No. 11/929,480, entitled "Method for developing, testing and using associates of macromolecules and complex aggregates for improved payload and controllable de/association rates", filed Oct. 30, 2007.

U.S. Appl. No. 11/667,325. entitled "Extended surface aggregates in the treatment of skin conditions", filed May 8, 2007.

U.S. Appl. No. 09/555,986, entitled "Method for developing, testing and using associates of macromolecules and complex aggregates for improved payload and controllable de/association rates", filed Aug. 17, 2000.

Prof. Dr. K-U Benner, "Der Korper des Menschen", p. 49 (1995).

Hans Schreier, "Liposomen—ein neuartiger Arzneistofftrager", Pharmazie in unserer Zeit, pp. 97-108 (1982).

Reviews on Biomembranes, Biochimica et Biophysica Acta, vol. 415 No. 1, pp. 29-79 (1975).

* cited by examiner

NSAID FORMULATIONS, BASED ON HIGHLY ADAPTABLE AGGREGATES, FOR IMPROVED TRANSPORT THROUGH BARRIERS AND TOPICAL DRUG DELIVERY

The present application claims the benefit of U.S. provisional application No. 60/417,847 filed on Oct. 11, 2002, incorporated herein by reference in its entirety.

FIELD OF INVENTION

This invention deals with novel formulations of nonsteroidal anti-inflammatory drugs (NSAIDs) based on complex, extended surface aggregates comprising at least three amphipatic components. One of these components is capable of forming stable, large bilayer membranes on it's own. The other at least two amphipatic components, including an NSAID, tend to destabilise such membranes. Said aggregates are normally suspended in a suitable, e.g. pharmaceutically acceptable, polar liquid medium, which also affects NSAID ionisation. The selection of the second amphipatic membrane destabilising component, which is typically a (co)surfactant, can boost the deformability of the resulting mixed extended surface aggregates. This effect may be supported by judicious choice of the other system components. The invention enables an improvement of barrier penetration and drug delivery by such aggregates. The invention also teaches how to select most appropriate NSAID concentration, the right total amphipat concentration and, in case, amphipat ionisation in the resulting mixed aggregate suspension. The invention further relates to preparation and application of the resulting suspension in pharmaceutical formulations, with a focus on epicutaneous application on, or less frequently in, warm blooded creatures.

BACKGROUND INFORMATION

The current state of the art in NSAID delivery through the skin is transdermal drug diffusion, which is proportional to the drug concentration on the skin and inversely proportional to the skin barrier resistance, which is tantamount to saying that diffusion is proportional to the skin permeability.

Solubility of typical NSAIDs is in the range 1 µg/ml to between 0.5 mg/ml and 10 mg/ml for the pH range between 1 and 7.5. This corresponds to a few µM and up to a few tens of mM, high values being always measured in least acidic solutions (pH>>$pK_a$) where NSAIDs are partly or completely ionised, the solubility at pH<<$pK_a$ always being very low. To maximise diffusive NSAID transport through the skin one should therefore always use the highest tolerable pH, which can exceed the value of 9.

Taken the limitations of maximum NSAID solubility, attempts have been made to improve NSAID permeation (diffusion) through the skin by using permeability or permeation enhancers. Permeability enhancers increase NSAID flux through the barrier for a given drug concentration, but do not much affect the depth of drug distribution. Further, use of conventional lipid formulations on the skin does not affect this limitation.

For example, Henmi et al. 1994 (Chem Pharm Bull 42:651-655) used three different NSAIDs (ketoprofen, flurbiprofen and ibuprofen) in an oily gel, formed by hydrogenated soybean phospholipids (which forms very stiff membranes) and applied the preparation on the skin. The conclusion was that such lipids have no permeation enhancing effect for the skin but rather solubilise the test drug.

Burnham et al. 1998 (Clin J Sport Med 8:78-81) used a block co-polymer of polyethylene and an unspecified polypropylene glycol (pluronic), which generally is a poor membrane destabilising amphipat, to apply an NSAID on the skin. An unspecified lecithin based liposomal organo-gel (PLO) was furthermore used three times daily for one week, followed by a weekly "washout" period without using the gel. The authors noted that only a thin tissue layer under the skin was treated, thus implying that any apparently positive result could be due to free drug diffusion from PLO through the skin. Organo-gel consequently has served as merely a superficial reservoir.

Vyas et al. (J Microencapsul 12:149-54, 1995) incorporated diclofenac into multilamellar, 1-5 µm large liposomes at pH=7.4 that were applied on the skin under different conditions. The resulting systemic drug availability was then studied. The resulting mixed lipid vesicles were incorporated in an ointment base and were applied on the skin of rats. However, skin poration by ultrasound was required to achieve any substantial transdermal delivery of the drug, and most of the tested NSAID was typically found at the site of application.

Schramlova et al. (Folia Biol (Praha) 43:195-199, 1997) associated ibuprofen with liposomes prepared from soybean phospholipid supplemented with 10 rel-% cholesterol, the knowledge in the art being that the latter is a membrane stiffening agent. The formulation with a pH=7.4 was injected intramuscularly or applied under occlusion on the skin. NSAID from lipid vesicles occasionally decreased the rat leg edema slightly, but not significantly, better than the drug from a conventional cream but less than an NSAID injection. This paper therefore teaches the use of a membrane stabilising component (cholesterol) rather than of a membrane destabilising component.

Saunders et al. (J Pharm Pharm Sci 2:99-107, 1999), studying the skin permeation enhancement, also used liposomal structures of unspecified composition and morphology, which were claimed to be present in the MZL lotion and in a comparator gel (both prepared by Meyer Zall Laboratories (MZL)), and loaded with sodium diclofenac. The presence of oil in the oil/water base in the MZL formulation, which diminishes lipid aggregate deformability, and occludes the skin, if nothing else precluded efficient drug delivery by vesicle through the skin.

Calpena et al. (Arzneimiftelforschung 49:1012-1017, 1999) studied diclofenac permeation through human skin from 6 semisolid formulations containing 1% drug in a complex mixture of gel-forming materials combined with lecithin (2.5% of unspecified quality) and cholesterol (0.5%). However, the results of the studies suggest that use of lipid vesicles is not beneficial (Calpena et al., 1999).

Skin permeability data for ibuprofen lysinate was studied, showing practically equal permeability rates for the drug in solution or in mixed micelles (containing soy-bean phosphatidylcholine) and nearly 3-times lower rate for the corresponding liposomal dispersion (Stoye et al., 1998 (Eur J Pharm Biopharm 46:191-200). Liposomes therefore were concluded to be useless in terms of supporting transdermal drug transport in the described system.

SUMMARY OF THE INVENTION

We have found, unexpectedly, that various combinations of at least two amphipatic components one of which is an NSAID, which can substantially destabilise a lipid-based, otherwise stable extended surface aggregate, typically in the form of a bilayer membrane, can synergistically increase the resulting at least three-component aggregate adaptability. In parallel, the aggregate (membrane) shape deformability is synergistically augmented. Consequently, the flux of such aggregate suspension through narrow pores is increased and/or the characteristic pressure that drives certain flux through the corresponding porous barrier is lowered.

The capability of said at least three-component aggregates to move through a semi-permeable barrier is thus facilitated. This finding is surprising given that the droplets covered by a bi-component bilayer membrane already have an appreciable barrier crossing capability compared to droplets enclosed by a simple lipid bilayer.

The increase of adaptability of said extended surface aggregates with at least three amphipatic components and/or the lowering of the pressure that is needed to make such aggregates move through a biological barrier has important, and unexpected, practical consequences. Specifically, when said aggregates are applied on the skin, as an example for a biological semi-permeable barrier, the transport of the aggregate associated NSAIDs through such barrier is increased and reaches further. The latter observation is explicable in terms of differential clearance in the superficial skin layers, where cutaneous blood drainage resides, of the drug, which can enter directly into blood capillaries, and of drug-loaded aggregates, which are too big to enter such capillaries. This means that NSAID carriers move further than the drug from solution, allowing deeper tissues to be treated with NSAIDs under the drug application site on the skin. Convincing evidence for this is given in one of Practical Examples. Such finding is not expected taken that simple NSAID-phospholipid combinations already ensure better and deeper drug transport through the skin than conventional preparations based on NSAID solutions.

In the present invention, the general terms employed hereinbefore and hereinafter have the following meanings.

The term "aggregate" denotes a group of more than just a few amphipats of similar or different kind. Typically, an aggregate referred to in this invention contains at least 100 molecules, i.e. has an aggregation number $n_a > 100$. More often aggregation number is $n_a > 1000$ and most preferably $n_a > 10.000$. An aggregate comprising an aqueous core surrounded with at least one lipid (bilayer) membrane is called a lipid vesicle, and often a liposome.

The term aggregate "adaptability" is defined in this document as the ability of a given aggregate to change easily, and more or less reversibly, its properties, such as shape, elongation ratio, and surface to volume ratio. Adaptability also implies that an aggregate can sustain unidirectional force or stress, such as a hydrostatic pressure, without significant fragmentation, as is defined for the "stable" aggregates. An easy and reversible change in aggregate shape furthermore implies high aggregate deformability and requires large surface-to-volume ratio adaptation. For vesicular aggregates, the latter is associated with material exchange between the outer and inner vesicle volume, i.e. with at least transient vesicle membrane permeabilisation. The experimentally determined capability of given aggregate suspension to pass through narrow pores in a semi-permeable barrier thus offers simple means for functionally testing aggregate adaptability and deformability (vide supra), as is described in the Practical Examples.

To assess aggregate adaptability it is useful to employ the following method:

1) measure the flux $j_a$ of aggregate suspension through a semi-permeable barrier (e.g. gravimetrically) for different transport-driving trans-barrier pressures delta p;

2) calculate the pressure dependence of barrier penetrability P for the given suspension by dividing each measured flux value with the corresponding driving pressure value: P (delta p)=$j_a$ (delta p)/delta p;

3) monitor the ratio of final and starting vesicle diameter $2r_{ves}$ (delta p)/$2r_{ves,0}$ (e.g. with the dynamic light scattering), wherein $2r_{ves}$ (delta p)/is the vesicle diameter after semi-permeable barrier passage driven by delta p and $2r_{ves,0}$ is the starting vesicle diameter, and if necessary making corrections for the flow-rate effects;

4) align both data sets P (delta p) vs. $r_{ves}$ (delta p)/$r_{ves,0}$, to determine the co-existence range for high aggregate adaptability and stability; it is also useful, but not absolutely essential, to parameterise experimental penetrability data within the framework of Maxwell-approximation in terms of the necessary pressure value p* and of maximum penetrability value $P_{max}$, which are defined graphically in the following illustrative schemes.

It is plausible to sum-up all the contributions to a moving aggregate energy (deformation energy/ies, thermal energy, the shearing work, etc.) into a single, total energy. The equilibrium population density of aggregate's energetic levels then may be taken to correspond to Maxwell's distribution. All aggregates with a total energy greater than the activation energy, E $f$ $E_A$, are finally concluded to penetrate the barrier. The pore-crossing probability for such aggregates is then given by:

$$P(e) = 1 - erf\left(\sqrt{\frac{1}{e}}\right) + \sqrt{\frac{4}{\pi e}} \cdot \exp\left[-\frac{1}{e}\right],$$

e being dimensionless aggregate energy in units of the activation energy $E_A$.

It is therefore plausible to write barrier penetrability to a given suspension as a function of transport driving pressure (=driving pressure difference) p (=delta p) as:

$$P(p) = p_{max} \cdot \left\{1 - erf\left(\sqrt{\frac{p^*}{p}}\right) + \sqrt{\frac{4p^*}{\pi p}} \cdot \exp\left[-\frac{p^*}{p}\right]\right\} \quad (*)$$

$P_{max}$ is the maximum possible penetrability of a given barrier. (For the aggregates with zero transport resistance this penetrability is identical to the penetrability of the suspending medium flux.) p* is an adjustable parameter that describes the pressure sensitivity, and thus the transport resistance, of the tested system. (For barriers with a fixed pore radius this sensitivity is a function of aggregate properties solely. For non-interacting particles the sensitivity is dominated by aggregate adaptability, allowing to make the assumption: $a_a$ proportional to 1/p*.)

The formula (*), is used in various Practical Examples to calculate aggregate adaptability from suspension flux, or more precisely from the corresponding penetrability (=P(p)=Flux/Pressure=Flux/p data).

This formula is explained, in more detail, in our copending U.S. application entitled "Aggregates with increased deformability, comprising at least three amphipats, for improved transport through semi-permeable barriers and for the non-invasive drug application in vivo, especially through the skin", filed concurrently, the disclosure of which is incorporated herein by reference.

The term "apparent dissociation constant" ("pKa") refers to the measured dissociation (i.e. ionisation) constant of a drug. This constant for many drugs, including NSAIDs, is different in the bulk and in the homo- or heteroaggregates. For ketoprofen, the pKa in the bulk is approx. 4.4 whereas the pKa value measured above the drug association concentration is approx. 5, and decreases approximately linearly with the inverse ionic strength of the bulk solution. pKa of ketoprofen bound to lipid bilayers increases with total lipid concentration as well, and is approx. 6 and 6.45 in suspensions with 5 w-% and 16 w-% total lipid in a 50 mM monovalent buffer, respectively. For diclofenac, the pKa in the bulk is around 4, whereas for this drug in lipid bilayers pKa~6.1 was determined. The bulk pKa reported in the literature for meloxicam, piroxicam, naproxen, indomethacin and ibuprofen is 4.2 (and 1.9), 5.3, 4.2-4.7, 4.5, and 4.3 (or in some reports 5.3), respectively.

The term aggregate "deformability" is closely related to the term "adaptability". Any major change in aggregate shape that does not result in a significant aggregate fragmentation is indicative of sufficient aggregate deformability, and also implies a large change in the deformed aggregate surface-to-volume ratio. Deformability can therefore be measured in the same kind of experiments as is proposed for determining aggregate adaptability, or else can be assessed by optical measurements that reveal reversible shape changes.

The term "long" used in connection with a fatty residue attached to a lipid, a surfactant or a drug implies the presence of 10 to 24 carbon atoms in alkyl, alkenyl, alkoxy, alkenyloxy or acyloxy chains, which individually or together, as the case may be, bear the class name of "fatty chains". Implicitly included in this term, but not further specified in detail, are "fatty chains" with at least one branched or a cyclic, but unpolar or little polar, segment.

The term "narrow" used in connection with a pore implies that the pore diameter is significantly, typically at least 30%, smaller than the diameter of the entity tested with regard to its ability to cross the pore.

The term "NSAID" (nonsteroidal anti-inflammatory drug) typically indicates a chemical entity which acts as lipoxygenase, cyclooxygenase-1 or cyclooxygenase-2 antagonist.

Examples include salts of substituted phenylacetic acids or 2-phenylpropionic acids, such as alclofenac, ibufenac, ibuprofen, clindanac, fenclorac, ketoprofen, fenoprofen, indoprofen, fenclofenac, diclofenac, flurbiprofen, pirprofen, naproxen, benoxaprofen, carprofen or cicloprofen; analgesically active heteroarylacetic acids or 2-heteroarylpropionic acids having a 2-indol-3-yl or pyrrol-2-yl radical, for example indomethacin, oxmetacin, intrazol, acemetazin, cinmetacin, zomepirac, tolmetin, colpirac or tiaprofenic acid; analgesically active indenylacetic acids, for example sulindac; analgesically active heteroaryloxyacetic acids, for example benzadac; NSAIDS from oxicame family include piroxicam, droxicam, meloxicam, tenoxicam; further interesting drugs from NSAID class are, meclofenamate, and the like. A list of commonly used NSAIDs is given in the following table:

| NSAID | Some common trade names |
|---|---|
| Acetaminofene | Tylenol |
| Cimicifuga | Artrol |
| Choline salicylate-Mg salicylate | Trilisate |
| Diclofenac | as Na salt: Apo-Diclo, Apo-Diclo SR, Arthrotec, Diclofenac Ect, Novo-Difenac, Novo-Difenac SR, Nu-Diclo, Taro-Diclofenac, Voltaren, Voltaren SR; as K salt: Voltaren Rapide |

-continued

| NSAID | Some common trade names |
|---|---|
| Diflunisal | Apo-Diflunisal, Dolobid, Novo-Diflunisal, Nu-Diflunisal |
| Etodolac | Ultradol |
| Fenoprofen calcium | Nalfon |
| Floctafenine | Idarac |
| Flurbiprofen | Ansaid, Apo-Flurbiprofen FC, Froben, Froben SR, Novo-Flurprofen, Nu-Flurbiprofen |
| Ibuprofen | Actiprofen, Advil, Advil Cold & Sinus, Amersol, Apo-Ibuprofen, Excedrin IB, Medipren, Motrin, Motrin IB, Novo-Profen, Nuprin, Nu-Ibufrofen |
| Indomethacin | Apo-Indomethacin, Indocid, Indocid SR, Indolec, Novo-Methacin, Nu-Indo, Pro-Indo, Rhodacine |
| Ketoprofen | Apo-Keto, Apo-Keto-E, Novo-Keto, Novo-Keto-Ec, Nu-Ketoprofen, Nu-Ketoprofen-E, Orudis, Orudis E, Orudis SR, Oruvail, PMS-Ketoprofen, PMS-Ketoprofen-E, Rhodis, Rhodis-EC |
| Ketorolac tromethamine | Acular, Toradol |
| Magnesium salicylate | Back-Ese-M, Doan's Backache Pills, Herbogesic |
| Mefenamic acid | Ponstan |
| Nabumetone | Relafen |
| Naproxen | Apo-Naproxen, Naprosyn, aprosyn-E, Naxen, Novo-Naprox, Nu-Naprox, PMS-Naproxen; or in the sodium form: Anaprox, Anaprox DS, Apo-Napro-Na, Naproxin-Na, Novo-Naprox Sodium, Synflex, Synflex DS |
| Oxyphenbutazone | Oxybutazone |
| Phenylbutazone | Alka Phenyl, Alka Phenylbutazone, Apo-Phenylbutazone, Butazolidin, Novo-Butazone, Phenylone Plus |
| Piroxicam | Apo-Piroxicam, Feldene, Kenral-Piroxicam, Novo-Pirocam, Nu-Pirox, PMS-Piroxicam, Pro-Piroxicam, Rho-Piroxicam |
| Salsalate | Disalcid |
| Sodium salicylate | Apo-Sulin, Dodd's, Dodd's Extra-Strength, Sulindac, Clinoril, Novo-Sundac, Nu-Sulindac, Sulindac |
| Tenoxicam | Mobiflex |
| Tiaprofenic acid | Albert Tiafen, Apo-Tiaprofenic, Surgam, Surgam SR |
| Tolmetin sodium | Novo-Tolmetin, Tolectin |

The term "phospholipid" has, for example, the formula

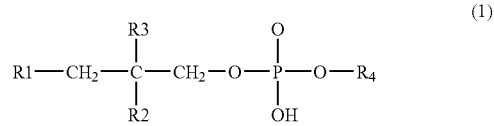

(1)

$$R_1-CH_2-\underset{\underset{R_2}{|}}{\overset{\overset{R_3}{|}}{C}}-CH_2-O-\underset{\underset{OH}{|}}{\overset{\overset{O}{\|}}{P}}-O-R_4$$

in which one of the radicals R1 and R2 represents hydrogen, hydroxy or C1-C4-alkyl, and the other radical represents a long fatty chain, especially an alkyl, alkenyl, alkoxy, akenyloxy or acyloxy, each having from 10 to 24 carbon atoms, or both radicals R1 and R2 represent a long fatty chain, especially an alkyl, alkenyl, alkoxy, alkenyloxy or acyloxy each having from 10 to 24 carbon atoms, R3 represents hydrogen or C1-C4-alkyl, and R4 represents hydrogen, optionally substituted C1-C7-alkyl or a carbohydrate radical having from 5 to 12 carbon atoms or, if both radicals R1 and R2 represent hydrogen or hydroxy, R4 represents a steroid radical, or is a salt thereof. The radicals R1, R2, R3, and R4 are typically selected so as to ensure that lipid bilayer membrane is in the fluid lamellar phase during practical application and is a good match to the drug of choice.

In a phospholipid of the formula 1, R1, R2 or R3 having the meaning C1-C4-alkyl is preferably methyl, but may also be ethyl, n-propyl, or n-butyl.

The terms alkyl, alkenyl, alkoxy, akenyloxy or acyloxy have their usual meaning. The long fatty chains attached to a phospholipid can also be substituted in any of usual ways.

A steroid radical R4 is, for example, a sterol radical that is esterified by the phosphatidyl group by way of the hydroxy group located in the 3-position of the steroid nucleus.

If R4 represents a steroid radical, R1 and R2 are preferably hydroxy and R3 is hydrogen.

Phospholipids of the formula 1 can be in the form of free acids or in the form of salts. Salts are formed by reaction of the free acid of the formula II with a base, for example a dilute, aqueous solution of alkali metal hydroxide, for example lithium, sodium or potassium hydroxide, magnesium or calcium hydroxide, a dilute aqueous ammonia solution or an aqueous solution of an amine, for example a mono-, di- or tri-lower alkylamine, for example ethyl-, diethyl- or triethylamine, 2-hydroxyethyl-tri-C1-C4-alkyl-amine, for example choline, and a basic amino acid, for example lysine or arginine.

A phospholipid of the formula 1 has especially two acyloxy radicals R1 and R2, for example alkanoyloxy or alkenoyloxy, for example lauroyloxy, myristoyloxy, palmitoyloxy, stearoyloxy, arachinoyloxy, oleoyloxy, linoyloxy or linoleoyloxy, and is, for example, natural lecithin (R3=hydrogen, R4=2-trimethylammonium ethyl) or cephalin (R3=hydrogen, R4=2-ammonium ethyl) having different acyloxy radicals R1 and R2, for example egg lecithin or egg cephalin or lecithin or cephalin from soya beans, synthetic lecithin or cephalin having different or identical acyloxy radicals R1 and R2, for example 1-palmitoyl-2-oleoyl lecithin or cephalin or dipalmitoyl, distearoyl, diarachinoyl, dioleoyl, dilinoyl or dilinoleoyl lecithin or cephalin, natural phosphatidyl serine (R3=hydrogen, R4=2-amino-2-carboxyethyl) having different acyloxy radicals R1 and R2, for example phosphatidyl serine from bovine brain, synthetic phosphatidylserine having different or identical acyloxy radicals R1 and R2, for example dioleoyl-, dimyristoyl- or dipalmitoyl-phosphatidyl serine, or natural phosphatidic acid (R3 and R4=hydrogen) having different acyloxy radicals R1 and R2.

A phospholipid of the formula 1 is also a phospholipid in which R1 and R2 represent two identical alkoxy radicals, for example n-tetradecyloxy or n-hexadecyloxy (synthetic ditetradecyl or dihexadecyl lecithin or cephalin), R1 represents alkenyl and R2 represents acyloxy, for example myristoyloxy or palmitoyloxy (plasmalogen, R3=hydrogen, R4=2-trimethylammonium ethyl), R1 represents acyloxy and R2 represents hydroxy (natural or synthetic lysolecithin or lysocephalin, for example 1-myristoyl- or 1-palmitoyl-lyso-lecithin or -cephalin; natural or synthetic lysophosphatidyl serine, R3=hydrogen, R4=2-amino-2-carboxyethyl, for example lysophosphatidyl serine from bovine brain or 1-myristoyl- or 1-palmitoyl-lysophosphatidyl serine, synthetic lysophosphatidyl glycerine, R3=hydrogen, R4=CH$_2$OH—CHOH—CH$_2$—, natural or synthetic lysophosphatidic acid, R3=hydrogen, R4=hydrogen, for example egg lysophosphatidic acid or 1-lauroyl-, 1-myristoyl- or 1-palmitoyl-lysophosphatidic acid).

The term "semipermeable" used in connection with a barrier implies that a solution can cross transbarrier openings whereas a suspension of non-adaptable aggregates 150-200% larger than the diameter of such openings cannot achieve this. Conventional lipid vesicles (liposomes) made from any common phospholipid in the gel lamellar phase or else from any biological phosphatidylcholine/cholesterol 1/1 mol/mol mixture or else comparably large oil droplets, all having the specified relative diameter, are three examples for such non-adaptable aggregates.

The term sufficiently "stable" means that the tested aggregate does not change its diameter spontaneously or under reasonable mechanical stress (e.g. during passage through a semipermeable barrier) to a practically, most often pharmaceutically, unacceptable degree. A 20-40% change is considered acceptable; the halving of aggregate diameter or a 100% diameter increase is not.

The term "sterol radical" means, for example, the lanosterol, sitosterol, coprostanol, cholestanol, glycocholic acid, ergosterol or stigmasterol radical, is preferably the cholesterol radical, but can also be any other sterol radical known in the art.

The term "surfactant" also has its usual meaning. A long list of relevant surfactants and surfactant related definitions is given in EP 0 475 160 and U.S. Pat. No. 6,165,500 which are herewith explicitly included by reference and in appropriate surfactant or pharmaceutical Handbooks, such as *Handbook of Industrial Surfactants* or US Pharmacopoeia, Pharm. Eu. The following list therefore only offers a selection, which is by no means complete or exclusive, of several surfactant classes that are particularly common or useful in conjunction with present patent application. This includes ionised long-chain fatty acids or long chain fatty alcohols, long chain fatty ammonium salts, such as alkyl- or alkenoyl-trimethyl-, -dimethyl- and -methyl-ammonium salts, alkyl- or alkenoyl-sulphate salts, long fatty chain dimethyl-aminoxides, such as alkyl- or alkenoyl-dimethyl-aminoxides, long fatty chain, for example alkanoyl, dimethyl-aminoxides and especially dodecyl dimethyl-aminoxide, long fatty chain, for example alkyl-N-methylglucamides and alkanoyl-N-methylglucamides, such as MEGA-8, MEGA-9 and MEGA-10, N-long fatty chain-N,N-dimethylglycines, for example N-alkyl-N, N-dimethylglycines, 3-(long fatty chain-dimethylammonio)-alkanesulphonates, for example 3-(acyidimethylammonio)-alkanesulphonates, long fatty chain derivatives of sulphosuccinate salts, such as bis(2-ethylalkyl) sulphosuccinate salts, long fatty chain-sulphobetaines, for example acyl-sulphobetaines, long fatty chain betaines, such as EMPIGEN BB or ZWITTERGENT-3-16, -3-14, -3-12, -3-10, or -3-8, or polyethylen-glycol-acylphenyl ethers, especially nonaethylen-glycol-octylphenyl ether, polyethylene-long fatty chain-ethers, especially polyethylene-acyl ethers, such as nonaethylen-decyl ether, nonaethylen-dodecyl ether or octaethylene-dodecyl ether, polyethyleneglycol-isoacyl ethers, such as octaethyleneglycol-isotridecyl ether, polyethyleneglycol-sorbitane-long fatty chain esters, for example polyethyleneglycol-sorbitane-acyl esters and especially polyethylenglykol-monolaurate (e.g. Tween 20), polyethylenglykol-sorbitan-monooleate (e.g. Tween 80), polyethylenglykol-sorbitan-monolauroleylate, polyethylenglykol-sorbitan-monopetroselinate, polyethylenglykol-sorbitan-monoelaidate, polyethylenglykol-sorbitan-myristoleylate, polyethylenglykol-sorbitan-palmitoleinylate, polyethylenglykol-sorbitan-petroselinylate, polyhydroxyethylene-long fatty chain ethers, for example polyhydroxyethylene-acyl ethers, such as polyhydroxyethylene-lauryl ethers, polyhydroxyethylene-myristoyl ethers, polyhydroxyethylene-cetyl-stearyl, polyhydroxyethylene-palmityl ethers, polyhydroxyethylene-oleoyl ethers, polyhydroxyethylene-palmitoleoyl ethers, polyhydroxyethylene-linoleyl, polyhydroxyethylen-4, or 6, or 8, or 10, or 12-lauryl, miristoyl, palmitoyl, palmitoleyl, oleoyl or linoeyl ethers (Brij series), or in the corresponding esters, polyhydroxyethylen-laurate, -myristate, -palmitate, -stearate or -oleate, especially polyhydroxyethylen-8-stearate (Myrj 45) and polyhydroxyethylen-8-oleate, polyethoxylated castor oil 40 (Cremophor EL), sorbitane-mono long fatty chain, for example alkylate (Arlacel or Span series), especially as sorbitane-monolaurate (Arlacel 20, Span 20), long fatty chain, for example acyl-N-methylglucamides, alkanoyl-N-methylglucamides, especially decanoyl-N-methylglucamide, dodecanoyl-N-methylglucamide, long fatty chain sulphates, for example alkyl-sulphates, alkyl sulphate salts, such as lauryl-sulphate (SDS), oleoyl-sulphate; long fatty chain thioglucosides, such as alkylthioglucosides and especially heptyl-, octyl- and nonyl-beta-D-thioglucopyranoside; long fatty chain derivatives of various carbohydrates, such as pentoses, hexoses and disaccharides, especially alkyl-glucosides and maltosides, such as hexyl-, heptyl-, octyl-, nonyl- and decyl-beta-D-glucopyranoside or D-maltopyranoside; further a salt, especially a sodium salt, of cholate, deoxycholate, glycocholate, glycodeoxycholate, taurodeoxycholate, taurocholate, a fatty acid salt, especially oleate, elaidate, linoleate, laurate, or myristate, most often in sodium form, lysophospholipids, n-octadecylene-glycerophosphatidic acid, octadecylene-phosphorylglycerol, octadecylene-phosphorylserine, n-long fatty chain-glycero-phosphatidic acids, such as n-acyl-glycero-phosphatidic acids, especially lauryl glycero-phosphatidic acids, oleoyl-glycero-phosphatidic acid, n-long fatty chain-phosphorylglycerol, such as n-acyl-phosphorylglycerol, especially lauryl-, myristoyl-, oleoyl- or palmitoeloyl-phosphorylglycerol, n-long fatty chain-phosphorylserine, such as n-acyl-phosphorylserine, especially lauryl-, myristoyl-, oleoyl- or palmitoeloyl-phosphorylserine, n-tetradecyl-glycero-phosphatidic acid, n-tetradecyl-phosphorylglycerol, n-tetradecyl-phosphorylserine, corresponding-, elaidoyl-, vaccenyl-lysophospholipids, corresponding short-chain phospholipids, as well as all surface active and thus membrane destabilising polypeptides. Surfactant chains are typically chosen to be in a fluid state or at least to be compatible with the maintenance of fluid-chain state in carrier aggregates.

The term "surfactant like phospholipid" means a phospholipid with solubility, and other relevant properties, similar to those of the corresponding surfactants mentioned in this application, especially in the Claims 10 and 11. A non-ionic surfactant like phospholipid therefore should have water solubility, and ideally also water diffusion/exchange rates, etc., similar to those of a relevant non-ionic surfactant.

Quite detailed recommendations on the preparation of said combinations is given in EP 0 475 160 and U.S. Pat. No. 6,165,500, which are herewith included by reference, using filtering material with pore diameters between 0.01 μm and 0.1 μm, more preferably with pore diameters between 0.02 μm and 0.3 μm and even more advisable filters with pore diameters between 0.05 μm and 0.15 μm to homogenise final vesicle suspension, when filtration is used for the purpose. Other methods of mechanical homogenisation or for lipid vesicle preparation known in the art are useful as well.

The lipids and certain surfactants mentioned hereinbefore and hereinafter having a chiral carbon atom can be present both in the form of racemic mixtures and in the form of optically pure enantiomers in the pharmaceutical compositions that can be prepared and used according to the invention.

To manufacture a pharmaceutical formulation, it may advisable or necessary to prepare the product in several steps, changing temperature, pH, ion strength, individual component (e.g. membrane destabiliser, formulation stabiliser or microbicide) or total lipid concentration, or suspension viscosity during the process.

A list of relevant and practically useful thickening agents is given e.g. in PCT/EP98/08421, which also suggests numerous interesting microbicides and antioxidants; the corresponding sections of PCT/EP98/08421 are therefore included into the present application by reference. Practical experiments have confirmed that sulphites, such as sodium sulphite, potassium sulphite, bisulphite and metasulphite; and potentially other water soluble antioxidants, which also contain a sulphur or else a phosphorus atom (e.g. in pyrosulphate, pyrophosphate, polyphosphate, erythorbate, tartrate, glutamate, and the like or even L-tryptophan, ideally with a spectrum of activity similar to that of sulphites) offer some anti-oxidative protection to said formulations, final selection being subject to regulatory constraints. Any hydrophilic antioxidant should always be combined with a lipophilic antioxidant, however, such as BHT (butylated hydroxytoluene) or BHA (butylated hydroxyanisole).

In one important aspect of the present invention, the invention provides preparations, based on a suspension of extended surface aggregates in a liquid medium comprising at least one first amphipatic component; at least one second amphipatic component; at least one third amphipatic component, the first amphipatic component being a vesicle membrane forming lipid component, the second and third component being membrane destabilising components, wherein the third component is a non-steroidal anti-inflammatory drug (NSAID) such that said aggregates are capable of penetrating semipermeable barriers with pores at least 50% smaller than the average aggregate diameter before the penetration without changing their diameter by more than 25%.

It is another aspect of the invention suspensions of extended surface aggregates in a liquid medium are provided, comprising: at least one first amphipatic component; at least one second amphipatic component; at least one third amphipatic component; the first amphipatic component being an aggregate, typically a membrane, forming lipid component; the second and third component being aggregate, typically membrane, destabilising components; wherein the third component is a NSAID, such that the extended surfaces formed by the first and second component alone or else by the first and third component alone, the second or third component, respectively, being present at a relative concentration X, have a lower propensity to overcome barriers with pores having a diameter at least 50% smaller than the average aggregate diameter, before the pore crossing, than the extended surfaces formed by the first, second and third component together, if the second and third components are present at or below the combined relative concentration of X. More specifically, this e.g. means that: a) said extended surfaces formed by the first and second component alone, the second component being present at a relative concentration X, have a lower propensity to overcome barriers with the pores at least 50% smaller than the average aggregate diameter before the pore crossing than the extended surfaces formed by the first, second and third component, if the second and third components are present at or below a combined concentration of X; or else b) such extended surfaces formed by the first and third component alone, the third component being present at a relative concentration X, have a lower propensity to overcome barriers with the pores at least 50% smaller than the average aggregate diameter before the pore crossing than extended surfaces formed by the first, second and third component, the second and third components together being present at or below a concentration of X.

In yet another aspect of the invention extended surface aggregates suspended in a liquid medium are provided, comprising: at least one first amphipatic component; at least one second amphipatic component; at least one third amphipatic component; the first amphipatic component being a membrane forming lipid component; the second and third component being membrane destabilising components, such that the third component is a NSAID; and the inclusion of the second or third component to an otherwise two amphipatic-component mixture increases the suspension flux through the pores at least 50% smaller than the average aggregate diameter before the penetration in comparison with the flux of the suspension containing aggregates comprising merely the first and second or the first and third components, respectively. More specifically, the inclusion of the third component increases the flux of said suspension compared with the flux of the suspension containing simpler aggregates comprising merely the first and second component or else the inclusion of the second component increases the flux of said suspension compared with the flux of the suspension containing simpler aggregates comprising merely the first and third component.

In a further aspect of this invention extended surface aggregates suspended in a liquid medium comprise: at least one first amphipatic component; at least one second amphipatic component; at least one third amphipatic component; the first amphipatic component being a membrane forming lipid component; the second and third component being membrane destabilising components, such that the third component is a NSAID and that the addition of the second or third component to an originally two component mixture increases aggregate adaptability of the resulting extended surface aggregates with at least three components compared to the aggregates containing respective combinations of the first and the third or the first and the second components alone. More specifically, the inclusion of the third component increases the aggregate adaptability of an extended surface aggregate comprising the first and second components alone; or else, the inclusion of the second component increases the aggregate adaptability of an extended surface aggregate comprising the first and third components alone.

Yet another aspect of this invention provides extended surface aggregates suspended in a liquid medium, comprising: at least one first amphipatic component; at least one second amphipatic component; at least one third amphipatic component; the first amphipatic component being a membrane forming lipid component; the second and third component being aggregate destabilising components, such that the third component is an NSAID; and the inclusion of the second or third component to an otherwise two amphipatic component mixture lowers the driving pressure required for aggregate penetration of pores at least 50% smaller than the average aggregate diameter before the penetration in comparison with the aggregates comprising merely the first and second or the first and third components, respectively. More specifically, the inclusion of the second component lowers the driving pressure required for aggregate penetration of pores at least 50% smaller than the average aggregate diameter before the penetration in comparison with the aggregates comprising merely the first and third components; alternatively, the inclusion of the third component lowers the driving pressure required for aggregate penetration of pores at least 50% smaller than the average aggregate diameter before the penetration in comparison with the aggregates comprising merely the first and second components.

It is a further aspect of this invention to provide extended surface aggregates suspended in a liquid medium, comprising: at least one first amphipatic component; at least one second amphipatic component; at least one third amphipatic component; the first amphipatic component being a membrane forming lipid component; the second and third component being membrane destabilising components, such that the third component is an NSAID and the inclusion of the second or third component to an otherwise two amphipatic component mixture increases the deformability of extended surface aggregates compared with the aggregates comprising merely the first and second or the first and third component, respectively. More specifically, the inclusion of the third component increases the deformability of the extended surface aggregates compared with the aggregates comprising merely the first and second component; alternatively, the inclusion of the second component increases the deformability of the extended surface aggregate compared with the aggregates comprising merely the first and third component.

The invention teaches preparation and use of said extended surface aggregates in the form of membrane-enclosed, liquid-filled vesicles, whereby said first component is a membrane-forming lipid, and said second and third components are membrane-destabilising components.

The invention includes suspensions of extended surface aggregates in a liquid medium comprising: at least one first amphipatic component; at least one second amphipatic component; at least one third amphipatic component; the first amphipatic component being a membrane forming lipid component; the second and third component being membrane destabilising components, such that the third component is a non-steroidal anti-inflammatory drug (NSAID) and such that said extended surface aggregates can penetrate intact mammalian skin, thus increasing NSAID concentration in the skin and/or increasing the reach of NSAID distribution below the skin, in comparison with the result of the same NSAID application in a solution on the skin. In a special version of said suspensions, said extended surface aggregates are membrane-enclosed, liquid-filled vesicles, said first component is a membrane-forming lipid, and said second and third components are membrane-destabilising components.

It is also an aspect of this invention to provide said suspensions wherein the third component is an NSAID, as defined above, most preferably is ketoprofen, ibuprofen, diclofenac, indomethacin, naproxen or piroxicam. To prepare said suspensions with these or other NSAID ingredients, the first, stable membranes forming, component is selected from the group consisting of lipids, lipoids from a biological source, corresponding synthetic lipids or lipoids, or modifications thereof. In this context it is preferable to choose amongst glycerides, glycolipids, glycerophospholipids, isoprenoidlipids, sphingolipids, steroids, sterines or sterols, sulphur-containing lipids, lipids containing at least one carbohydrate residue, or other polar fatty derivatives. Specifically, the preferred choice are the groups of phosphatidylcholines, phosphatidylethanolamines, phosphatidylglycerols, phosphatidylinositols, phosphatidic acids, phosphatidylserines, sphingomyelins, sphingophospholipids, glycosphingolipids, cerebrosides, ceramidpolyhexosides, sulphatides, sphingoplasmalogenes, or gangliosides.

It is a further aspect of this invention to teach that the first suspension component is preferably selected amongst lipids with one or two, not necessarily identical, fatty chains, especially with acyl-, alkanoyl, alkyl-, alkylene-, alkenoyl-, alkoxy, or chains with omega-cyclohexyl-, cyclo-propane-, iso- or anteiso-branched segments, or the corresponding chains mixtures. Useful chains include n-decyl, n-dodecyl (lauryl), n-tetradecyl(myristyl), n-hexadecyl(palmityl), n-octadecyl(stearyl), n-eicosyl(arachinyl), n-docosyl(behenyl) or n-tetracosyl(lignoceryl), 9-cis-dodecenyl(lauroleyl), 9-cis-tetradecenyl(myristoleyl), 9-cis-hexadecenyl(palmitoleinyl), 9-cis-octadecenyl(petroselinyl), 6-trans-octadecenyl (petroselaidinylj, 9-cis-octadecenyl(oleyl), 9-trans-octadecenyl(elaidinyl), 9-cis-eicosenyl(gadoleinyl), 9-cis-docosenyl (cetoleinyl) or n-9-cis-tetracosoyl(nervonyl), n-decyloxy, n-dodecyloxy(lauryloxy), n-tetradecyloxy(myristyloxy), n-hexadecyloxy(cetyloxy), n-octadecyloxy(stearyloxy), n-eicosyloxy(arachinyloxy), n-docosoyloxy(behenyloxy) or n-tetracosoyloxy(lignoceryloxy), 9-cis-dodecenyloxy(lauroleyloxy), 9-cis-tetradecenyloxy(myristoleyloxy), 9-cis-hexadecenyloxy(palmitoleinyloxy), 6-cis-octadecenyloxy, (petroselinyloxy), 6-trans-octadecenyloxy(petroselaidinyloxy), 9-cis-octadecenyloxy(oleyloxy), 9-trans-octadecenyloxy(elaidinyloxy), and 9-cis-eicosenyl(gadoleinyloxy), 9-cis-docosenyl(cetoleinyloxy) or n-9-cis-tetracosoyl(nervonyloxy), n-decanoyloxy, n-dodecanoyloxy(lauroyloxy), n-tetradecanoyloxy(myristoyloxy), n-hexadecanoyloxy (palmitoyloxy) I n-octadecanoyloxy(stearoyloxy), n-eicosanoyloxy(arachinoyloxy), n-n-docosoanyloxy(behenoyloxy) and n-tetracosanoyloxy(lignoceroyloxy), 9-cis-dodecenyloxy(lauroleoyloxy), 9-cis-tetradecenoyloxy (myristoleoyloxy), 9-cis-hexadecenoyloxy (palmitoleinoyloxy), 6-cis-octadecenoyloxy (petroselinoyloxy), 6-trans-octadecenoyloxy (petroselaidinoyloxy), 9-cis-octadecenoyloxy(oleoyloxy), 9-trans-octadecenoyloxyelaidinoyloxy), and 9-cis-eicosenoyloxy(gadoleinyloxy), 9-cis-docosenoyloxy(cetoleinoyloxy) and 9-cis-tetracosenoyloxy(nervonoyloxy) or the corresponding sphingosine derivative chains, or corresponidng two double bonds combinations, especially in the sequence 6,9-cis, 9,12-cis or, in case, 12,15-cis or else the related three double bonds combinations, especially in the sequence, 6,9, 12-cis, or 9,12,15-cis are preferable. A preferred choice in case of phosphatidylcholines of biological, and preferably plant, origin, is to use the lipids extracted from soy (bean), coconut, olive, safflower or sunflower, linseed, evening primrose, primrose, castor oil, and the like.

According to the invention the second suspension component, which tends to destabilise lipid membranes, is preferably a surfactant. The selected surfactant can belong to the group of nonionic, zwitterionic, anionic and cationic surfactants. Preferentially, any such surfactant is chosen to have solubility in the liquid medium ranging from about $5 \times 10^{-7}$ M to about $10^{-2}$ M. An alternative definition of surfactants useful for the use in said suspensions of extended surface aggregates relates to hydrophilicity-lipophilicity ratio (HLB), which should be between 10 and 20, preferably between 12 and 18 and most preferred between 13 and 17. A good choice of non-ionic surfactants according to this invention are polyethyleneglycol-sorbitan-long fatty chain esters, from polyethyleneglycol-long fatty chain esters or -ethers and from polyhydroxyethylen-long fatty chain esters or -ethers; preferably, the number of ethyleneglycol or hydroxyethylen units per such surfactant molecule is selected to be in the range 6 to 30, more conveniently to be between 8 and 25 and most and typically to be between 12 to 20. Alternatively, non-ionic phospholipids with water solubility similar to that of said non-ionic surfactants, can be used to the same effect. Examples include lyso-phospholipids, certain phosphatidylglycerols, phospholipids with one long and one short (C1-C6) chain, and the like. In order to ensure sufficient fluidity of resulting complex extended surface aggregates, the hydrophobic chain attached to such polar groups is preferentially chosen to be sufficiently short or to be unsaturated; polyethylenglycol-sorbitan-monolaurate and polyethylenglycol-sorbitan-monooleate, polyethyleneglycol-monolaurate and polyethyleneglycol-monooleate or polyethyleneglycol-monolaurate-ether and polyethyleneglycol-monooleate-ether are good choices in this respect. More specifically, it is preferable in the context of this invention, to use a surfactant which is polyethyleneglycol-sorbitan-monooleate or monolaurate (e.g. Tween 80 or Tween 20) or else is polyethyleneglycol-oleate or laurate (i.e. POE-oleate or POE-laurate) or else is polyethyleneglycol-oleyl-ether or lauryl-ether, with 6 to 30, more preferably 8 to 15 and most preferred 12 to 20 ethyleneglycol (i.e. oxyethylene or OE) units per surfactant molecule.

It is another aspect of this invention to combine, in said suspension, a phosphatidylcholine as the first component and ketoprofen, diclofenac, ibuprofen, indomethacin, naproxen, or piroxicam as the third NSAID component. A preferred choice is the combination of soy phosphatidylcholine as the first and of ketoprofen, diclofenac, ibuprofen, indomethacin, naproxen or piroxicam as the third component.

In a preferred embodiment of the invention, the second component is a non-ionic surfactant, such as a polyethyleneglycol-sorbitan-long fatty chain ester, a polyethyleneglycol-long fatty chain ester or a polyethyleneglycol-long fatty chain ether or else the corresponding surfactant with a polyhydroxyethylene polar group. A preferred choice is the use of polyethyleneglycol-sorbitan-monooleate or -laurate, of polyethyleneglycol-monooleate or -laurate, or else of polyethyleneglycol-oleyl-ether or -lauryl-ether as the second component. In the resulting suspension, the second component is preferablely chosen to carry a polyethyleneglycol (PEG or POE) polar head with 6 to 30, more preferably 8 to 15 and most preferred 12 to 20 ethyleneglycol (i.e. oxyethylene or OE) units per surfactant molecule. Alternatively, non-ionic phospholipids, with water solubility similar to that of said non-ionic surfactants can be used for similar purpose. Moreover, the hydrophobic chains are chosen to be in a fluid state or at least to be compatible with such state of a carrier aggregate.

In another preferred embodiment of this invention is to provide said suspensions that contain aggregates with an average diameter before the aggregates penetrate the pores, at least 40% larger than the average pore diameter in the barrier of interest.

In a preferred embodiment of the invention, extended surface aggregates are proposed to have an average aggregate diameter that is at least 50% larger before pore penetration than the average pore diameter. Preferably, the average aggregate diameter before the aggregates penetrate the pores is at least 70%, even more preferably is at least 100% and most preferably is at least 150% larger than the average pore diameter.

Another aspect of the invention is to provide suspensions in which the first component and the second component differ in solubility in the liquid medium at least 10-fold, on the average. The preferred difference in solubility between the second and third component is, on the average, at least 2-fold.

In a further preferred embodiment of the invention said suspension comprises a total dry mass of the at least three amphipatic components between 0.01 weight-% and 50 weight-%. A more preferred choice is to keep this total dry mass between 0.1 weight-% and 40 weight-%, better to keep even it between 0.5 weight-% and 30 weight-% and best to select the total dry mass of the three amphipatic components between 1 weight-% and 15 weight-%, at the time of formulation preparation and/or application.

Yet another aspect of the invention is to provide suspensions of extended surface aggregates, formed by the three components, with an average curvature corresponding to the average aggregate diameter between 15 nm and 5000 nm, preferably between 30 nm and 1000 nm, more preferred between 40 nm and 300 nm and most preferred between 50 nm and 150 nm.

Another aspect of the invention is to advocate using suspensions of extended surface aggregates that contain a lower aliphatic alcohol with a membrane partition coefficient and polarity such that the alcohol, as the at least one further second component, takes the role of a membrane destabilising component. Alcohols that potentially qualify for such use include mono-alcohols, diols, or to some extent polyols, of low carbon number (C1-C6), and ethers thereof; preferred examples are ethanol, isopropanol, 1,2-propanediol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products. The preferred choice are simple alcohols, short chain diols or a short chain triols, preferably with the OH-residues grouped together, corresponding methyl-, ethyl-, or butyl-derivatives also being a possibility. This includes especially n-propanol, iso-propanol, or 2-propanol, n-butanol, or 2-butanol, 1,2-propanediol, 1,2-butanediol; if ethanol is used, the total alcohol and lipid concentration are selected such that practically useful ethanol association with a pQre penetrating aggregate is ensured. Specifically, if used individually to increase extended surface aggregate adaptability, ethanol, n-propanol, 2-propanol, butanol, and benzyl alcohol are preferably used at concentrations up to 15 w-%, 10 w-%, 8 w-%, 4 w-% and 2 w-%, respectively, in case of an initially 10 w-% total lipid suspension. The published water-membrane partition coefficients for other alcohols can be used together with these recommendations to select preferred concentration of other alcohols, or of alcohol combinations.

An important further aspect of the invention is to propose pharmaceutical preparations comprising suspensions according to the invention. A very convenient and preferred form of aggregates in such suspension is that of liquid-filled vesicles in an aqueous medium, the vesicles being enclosed by membranes formed from at least one lipid component and comprising at least two membrane destabilising components one of which is an NSAID, whereby the extended surfaces formed by the first and second component alone or else by the first and third component alone, the second or third component, respectively, being present at a relative concentration X, have a lower propensity to overcome barriers with pores at least 50% smaller than the average aggregate diameter before the pore crossing than the extended surfaces formed by the first, second and third component together, if the second and third components are present at or below the combined relative concentration of X.

It is also an important aspect of the invention, to teach pharmaceutical preparations comprising a suspension of liquid-filled vesicles in an aqueous medium, the vesicles being enclosed by membranes formed from at least one lipid component and comprising at least three membrane destabilising components, whereby the membrane destabilising components comprise at least one surfactant, at least one lower aliphatic alcohol and at least one non-steroidal anti-inflammatory drug; such that the membrane destabilising components increase the adaptability of the resulting extended surface aggregates with at least three components compared to the aggregates containing respective combinations of the first and the third or the first and the second components alone.

It is a further aspect of the invention to provide pharmaceutical preparations comprising a suspension of liquid-filled vesicles in an aqueous medium, the vesicles being enclosed by membranes formed from at least one lipid component and comprising at least three membrane destabilising components, whereby the membrane destabilising components comprise at least one surfactant, at least one lower aliphatic alcohol and at least one non-steroidal anti-inflammatory drug, such that the membrane destabilising components increase the deformability of the vesicles and the vesicles are capable of penetrating barriers with pores at least 50% smaller than the average aggregate diameter before the penetration without changing their diameter by more than 25%.

It is another aspect of the invention to provide pharmaceutical preparations comprising a suspension of liquid-filled vesicles in an aqueous medium, the vesicle being enclosed by membranes formed from at least one lipid component and comprising at least three membrane destabilising components, whereby the membrane destabilising components comprise a surfactant, a lower aliphatic alcohol and a non-steroidal anti-inflammatory drug, whereby the membrane destabilising components increase the vesicle ability to penetrate mammalian skin and thus increase the reach of NSAID distribution in the skin, and beyond, in comparison with the result of an NSAID application in a solution on the skin.

A preferred embodiment of the invention provides vesicle containing pharmaceutical preparations in which a phosphatidylcholine takes the role of first component and an NSAID, such as ketoprofen, diclofenac, ibuprofen indomethacin, naproxen, or piroxicam is the third component.

In another preferred embodiment of the invention pharmaceutical preparations contain a nonionic surfactant, preferably a polyethyleneglycol-sorbitan-long fatty chain ester, a polyethyleneglycol-long fatty chain ester or a polyethyleneglycol-long fatty chain ether, the polyethyleneglycol chain being potentially replaced by a polyhydroxyethylene polar group. Specifically preferred are polyethyleneglycol-sorbitan-monooleate (e.g. Tween 80) or -laurate (e.g. Tween 20), or else polyoxyethylene-monooleate (e.g. Cithrol 10MO/Chemax E-1000) or -laurate (e.g. Cithrol 10ML) or else polyoxyethylene-oleyl-ether (e.g. Brij 98) or -lauryl-ether (e.g. Brij 35). Alternatively, non-ionic phospholipids, with water solubility similar to that of said non-ionic surfactants, are used as a preferred nonionic surfactant.

In a related embodiment of the invention, said pharmaceutical preparations contain an alcohol, which preferably is selected from n-propanol, iso-propanol, 2-propanol, n-butanol or 2-butanol, 1,2-propanediol, or 1,2-butanediol, a methyl- or ethyl-derivative thereof, or ethanol. When ethanol is used, the total alcohol and lipid concentration is chosen to ensure a practically useful ethanol association with a pore penetrating aggregate.

It is also an aspect of the invention to provide such pharmaceutical preparations that are characterised by the bulk pH value above, the logarithm of the apparent dissociation constant (pKa) of the NSAID in a solution and in the extended surface aggregates, the latter pKa being higher than the former. Preferably, the bulk pH value is selected to be between 0.2 pH and 2.2 pH units above pKa of the NSAID in an extended surface aggregate, more preferably is between 0.5 pH and 1.9 pH units above this pKa and ideally is between 0.8 pH and 1.6 pH units above such pKa. Specifically, for the particularly interesting NSAIDs, ketoprofen or ibuprofen, the selected bulk pH is between 6.4 and 8.3, more preferably is between 6.7 and 8 and most preferably is between 7 and 7.7; for diclofenac the preferred bulk pH is between 6.2 and 8.1, more preferably is between 6.5 and 7.8 and most preferably is between 6.8 and 7.5; for naproxen the corresponding preferred pH value is between 6.3 and 8.2, more preferably is between 6.6 and 7.9 and most preferably is between 6.9 and 7.6; for piroxicam the choice of suspension bulk pH should be between 7.2 and 9, more preferably between 7.3 and 8.5 and most preferably between 7.4 and 8.2.

It is another aspect of the invention to select the bulk ionic strength of said pharmaceutical preparation is between 0.005 and 0.3, even better between 0.01 and 0.2 and best between 0.05 and 0.15.

In preferred embodiment of the invention the said pharmaceutical formulation has viscosity between 50 mPa s and 30.000 mPa s. Preferably, the formulation viscosity is chosen to be between 100 mPa s and 10.000 mPa s, even better between 200 mPa s and 5000 mPa s, and most preferred between 400 mPa s and 2000 mPa s. To achieve such viscosity, at least one thickening agent may be added to said pharmaceutical formulation, precise choice and concentration of such agent depending on the ambient temperature, pH, ion strength, presence of other viscosity modifiers (such as glycerol), etc.

Thickening agents that are useful in the context of present invention are typically pharmaceutically acceptable hydrophilic polymers, including partially etherified cellulose derivatives, such as carboxymethyl-, hydroxyethyl-, hydroxypropyl-, hydroxypropylmethyl- or methyl-cellulose; completely synthetic hydrophilic polymers, including polyacrylates , polymethacrylates, poly(hydroxyethyl)-, poly(hydroxypropyl)-, poly(hydroxypropylmethyl)methacrylate, polyacrylonitriles, methallyl-sulphonates, polyethylenes, polyoxiethylenes, polyethylene glycols, polyethylene glycol-lactides, polyethylene glycol-diacrylates, polyvinylpyrrolidones, polyvinyl alcohols, poly(propylmethacrylamide), poly(propylene fumarate-co-ethylene glycol), poloxamers, polyaspartamides, (hydrazine cross-linked) hyaluronic acids, silicone; natural gums, such as alginates, carrageenan, guar-gum, gelatine, tragacanth, (amidated)pectin, xanthan, chitosan collagen, agarose; mixtures and further derivatives or co-polymers thereof and/or other biologically acceptable polymers. Most of such thickening agents in said pharmaceutical preparation are employed in weight concentration between 0.1 w-% and 10 w-%.

For the use of pharmaceutical formulations of the invention, the following hydrophilic polymer are preferred, amongst others: partially etherified cellulose derivatives, such as carboxymethyl -, hydroxyethyl-, hydroxypropyl-cellulose or amongst completely synthetic hydrophilic polymer s from the class of polyacrylates, such as polymethacrylates, poly(hydroxyethyl)-, poly(hydroxypropyl)-, poly(hydroxypropylmethyl)methacrylate, especially Carbopols.

Most preferably, such formulation thickeners are chosen from the group of polysaccharides and derivatives thereof that are commonly used on the skin, including e.g. hyaluronic acid or hydroxypropylmethylcellulose; particularly preferable choices from the group of polyacrylates include the group of Carbopols, such as Carbopol grades 974, 980, 981, 1 382, 2 984, 5 984, in each case individually or in combination. In case of Carbopols (e.g. Carbopol 974), used to thicken the suspension-based multicomponent formulations for improving NSAID delivery through permeability barriers and the skin, the polymer concentration preferably is selected to be between 0.3 w-% and 5 w-%, better between 0.5 w-% and 3 w-% and best between 0.75 w-% and 1.75 w-%. Manufacturer's recommendations for obtaining certain viscosity can be combined with these guiding concentrations to use other polymers or polymer combinations in a formulation for similar purpose.

It is another preferred embodiment of the invention to use at least one antioxidant in said pharmaceutical formulations, which is typically selected amongst synthetic phenolic compounds and their derivatives, the quinone-group containing substances, aromatic amines, ethylenediamine derivatives, various phenolic acids, tocopherols and their derivatives, including the corresponding amide and thiocarboxamide analogues; ascorbic acid and its salts; primaquine, quinacrine, chloroquine, hydroxychloroquine, azathioprine, phenobarbital, acetaminephen; aminosalicylic acids and derivatives; methotrexate, probucol, sulphur or phosphate atom containing anti-oxidants, thiourea; chellating agents, miscellaneous endogenous defence systems, and enzymatic antioxidants, etc. Preferred are combinations of at least two antioxidants, one being lipophilic, such as butylated hydroxyanisol (BHA), butylated hydroxytoluene (BHT), di-tert-butylphenol, or tertiary butylhydroquinone (TBHQ), and the other being hydrophilic, such as a chellating agent, especially EDTA, GDTA, or desferral, and/or is a sulphite, such as sodium or potassium metabisulphite, a pyrosulphate, pyrophosphate or polyphosphate. The butylated hydroxyanisol (BHA) or hydroxytoluene (BHT) are typically used at concentrations between about 0.001 w-% and about 2 w-%, more preferably between about 0.0025 w-% and about 0.2 w-%, and most preferably is between about 0.005 w-% and about 0.02 w-%; EDTA or GDTA concentration is typically chosen between about 0.001 w-% and about 5 w-%, preferably between about 0.005 w-% and about 0.5 w-%, more preferably between about 0.01 w-% and about 0.2 w-% and most preferably between about 0.05 and about 0.975 w-%; a sulphite, such as sodium or potassium metabisulphite is used preferably used in concentration range between about 0.001 w-% and about 5 w-%, more preferably between about 0.005 w-% and about 0.5 w-%, and most preferably between about 0.01 w-% and about 0.15 w-%.

In preferred embodiments of the invention pharmaceutical preparations contain at least one microbicide in concentration range between about 0.1 w-% and about 5 w-%, as is required for proper action and as is acceptable by a regulatory body.

In presently preferred pharmaceutical preparations the first, i.e. phospholipid, component and the third, i.e. NSAID, components are present in the molar range between about 10/1 and about 1/1. A more preferred range molar range of these two components is between about 5/1 and about 2/1, or even between about 4/1 and about 2.5/1 and the most preferred composition have phospholipid/NSAID molar ratio near about 3/1.

Likewise, it is preferred according to the invention that the molar concentration ratio of the phospholipid component, which forms stable lipid membranes, and of the second, surfactant-like component, which destabilises such membranes, in said pharmaceutical preparations should be between about 40/1 and about 4/1. More preferably such a molar ratio is between about 30/1 and about 7.5/1, the ratios between about 20/1 and about 10/1 being most preferred.

It is a further aspect of the invention to provide a kit, comprising, in a tube or otherwise packaged form, at least one dose of the pharmaceutical preparation containing an NSAID associated with the aggregates suitable for overcoming biological barriers such as the skin.

It is another aspect of the invention to provide a method for treating peripheral pain and/or inflammation by applying said pharmaceutical preparation on the skin of a warm blooded mammal.

A further aspect of the invention is to select different formulation doses per area to control the depth of NSAID delivery, if desirable using a non-occlusive patch for the purpose.

In a special embodiment of the invention at least one dose of an NSAID in said pharmaceutical formulation is applied, and the application is repeated several, e.g. up to five times per day, if necessary, the preferred choice being two applications per day.

Last but not least, it is envisaged by the invention to use transdermal carriers, typically in the form of barrier penetrating extended surface aggregates, to deliver NSAIDs below the skin and into the underlying muscle tissue and/or the adjacent joints.

PRACTICAL EXAMPLES

The following examples illustrate the invention without limiting it. All temperatures are in degree Celsius. Carrier diameters are in nanometers, pressures are in Pascal (Pa) and other units correspond to the standard SI system. Ratios and percentages are given in moles, unless otherwise stated.

All measurements were done at room temperature, except when specified otherwise. For aggregate adaptability/barrier transport resistance measurements the test temperature was constant to within plus/minus 2 degrees. For aggregate diameter measurements the temperature accuracy was plus/minus 0.1 degree. The pH value of the bulk suspension was determined with a commercial (gel) electrode. Suspension viscosity was measured with a rotation viscosimeter, typically at room temperature and using 20 RPM, which corresponded to 150 1/s.

All substances were used as received and were of p.a. quality, unless stated otherwise. Molar masses were taken to be identical to the published reference data.

Aggregate Adaptability Determination was conveniently conducted by measuring the normalised penetrability of a semi-permeable barrier to test aggregate suspension, as is described in great detail in copending U.S. application entitled "Aggregates with increased deformability, comprising at least three amphipats, for improved transport through semi-permeable barriers and for the non-invasive drug application in vivo, especially through the skin", filed concurrently, the disclosure of which is already incorporated herein by above reference.

In short, aggregate adaptability is identified with the inverse pressure difference 1/p* needed to attain a predefined, practically relevant fraction of maximum achievable suspension flux-pressure ratio ($P_{max}$). Using 50-60% maximum penetrability criterion gives reasonable results. Specifically, all p* values given in this document correspond to 57% of $P_{max}$-value.

Exemplary results are given in FIGS. 1 and 2. The latter figure also graphically illustrates the meaning of parameters "p*" (in pressure units, and proportional to barrier transport resistance) and "Maximum penetrability" (=$P_{max}$; in flux per pressure units, and indicative of barrier porosity).)

Aggregate diameter determination. The average aggregate (most often vesicle) diameter was measured with the dynamic light scattering (for a few samples with a Malvern Zeta-Sizer instrument and for the majority of samples with the instrument with an ALV 5000 correlator. Cumulant analysis method are an implementation of software package "Contin" was used for the analysis of the correlation curves obtained with Zeta-Sizer. To analyse the ALV measurements the software delivered by the manufacturer (cumulant analysis or "Contin") was employed.

Examples 1-4

| Composition: | |
|---|---|
| 80.0-71.4 mg | Phosphatidylcholine from soy-bean (SPC) |
| 20-28.6 mg | Ketoprofen, sodium (KT), replacing SPC in the suspension to achieve constant amphipat amount |
| add 1 ml | Phosphate buffer, pH = 7.2, if necessary readjusted with NaOH |

Objective: to demonstrate that ketoprofen, an NSAID, acts as membrane destabilising component and can render mixed amphipat aggregates with extended surface adaptable enough to penetrate narrow pores.

Test suspension preparation. The stated phospholipid and drug amounts were brought into suspension using mechanical homogenisation. That resulting average aggregate diameter was around 100 nm. For reference, a comparable suspension containing SPC and sodium cholate in 3.75/1 mol/mol ratio was used.

Vesicle transport ability (pore penetration capability/adaptability). The efflux of the test suspension from a vessel pressurised with nitrogen gas was measured as a function of the time to determine the pressure dependency of material transport through the 20 nm pore filter in front of an opening in the measuring vessel. From the measured flux data, the effective "barrier penetrability", which defines the adaptability of the tested mixed amphipat vesicles, was calculated as is described in the main text body. The measured curves were also analysed in terms of the pressure p*, needed to achieve 57% of maximum possible suspension flux/pressure ratio. The calculated p*-value decreased from 2.41±0.15 MPa (mean value±standard error) through 1.66±0.07 MPa to 1.36±0.10 MPa with increasing drug concentration. This is indicative of membrane destabilising activity of the drug, which arguably promotes bilayer flexibility and permeability. More detailed information is given in Table 1, which reveals essentially identical p* values for the SPC/KT 3/1 mol/mol mixture and for the reference anionic Transfersome® suspension. To deduce vesicle adaptability from p*-value, contribution from suspension viscosity effects must be included or must be known to be negligible. This is not an issue, however, as long as one can make comparisons with suitable reference formulation(s), as is done in the following table by inclusion of the last row.

In this test series, and in all other practical examples reported herein, the final aggregate diameter after narrow pore crossing was at least 300%, and typically was more than 400% greater than the pore diameter, the final to starting aggregate diameter ratio being typically >0.70, implying fragmentation of less than 30%, and more often merely 10-20%.

TABLE 1

Fit results, based on eq. (*) for the barrier penetrability (flux/pressure ratio) experiments done with the suspensions characterised by different lipid/drug, SPC/KT ratios

| SPC/KT [mole/mole] | p* [MPa] | $P_{max}$ [$10^{-11}$ m Pa$^{-1}$ · sec$^{-1}$] | Adaptability $a_a$, [MPa$^{-1}$] |
|---|---|---|---|
| 10/0 | ~3 | Not measurable | ~0.3 |
| 4/1 | 2.41 ± 0.15[§] | Not measurable | 0.415 |
| 3/1 | 1.66 ± 0.07[§] | — | 0.602 |
| 2.5/1 | 1.36 ± 0.10[§] | 345 ± 37 | 0.735 |
| Reference anionic Tfs[§§] | 1.76 ± 0.13[§] | 318 ± 39 | 0.568 |

[§]The quoted error only accounts for analytical and not for experimental data uncertainty, the latter often amounting to 20-30%.
[§§]These Tfs vesicles were prepared from an SPC/Na cholate 3.75/1 mol/mol mixture.

Figure 1:
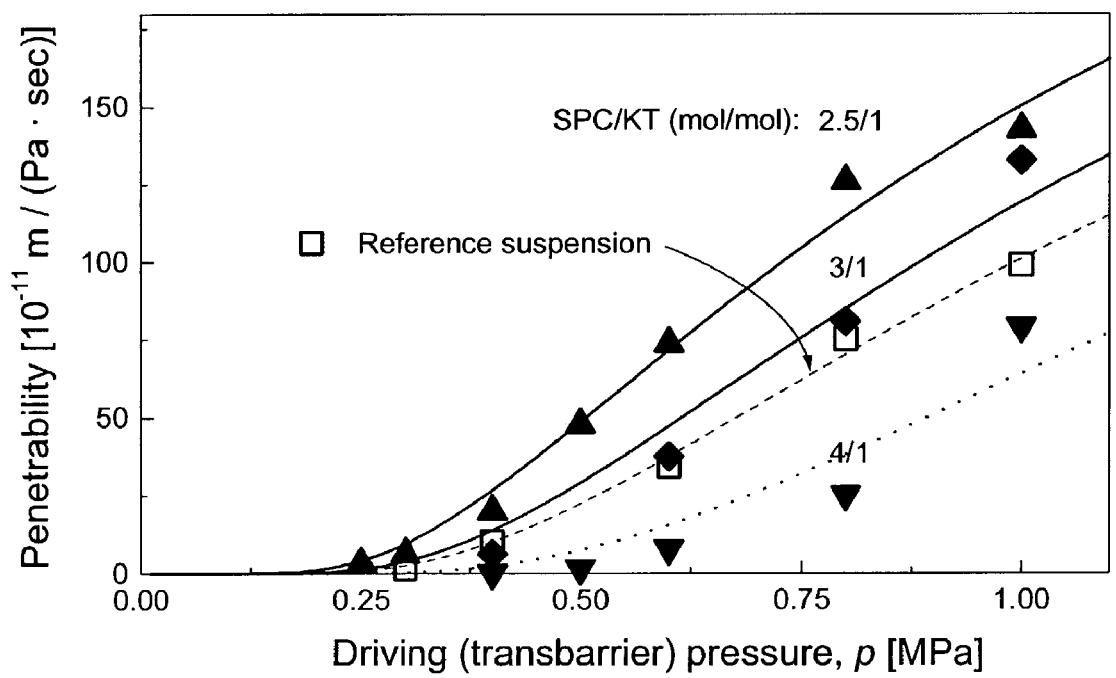
FIG. 1: Penetration curves for different SPC/KT mixtures: ·Δ·=2.5/1 SPC/KT, (3/1 SPC/KT, ∇ 4/1 SPC/KT, E SPC/Tween 1/1 Transfersomes® as a Reference suspension. The curves were calculated within the framework of data fitting model described in parallel application, by using eq. (*).

Graphic representation of the results of these experiments is given in FIG. 1.

Examples 5-7

| | Composition: |
|---|---|
| 75.0, 75.0, 37.7 mg | Phosphatidylcholine from soy-bean (SPC) |
| 25.0, 25.0, 0.0 mg | Ketoprofen, sodium (KT) |
| 0.0, 25.4, 62.3 mg | Tween 80 |
| 0.0, 0.0, 37.7 mg | Ethanol |
| add 1 ml | Phosphate buffer (pH = 7.2) |

Objective: to test the synergistic effect of the second and first membrane destabilising amphipat (Tween 80, ketoprofen, respectively) in terms of an extended surface aggregate adaptability.

Suspension preparation was essentially the same as with examples 1-4.

Figure 2:
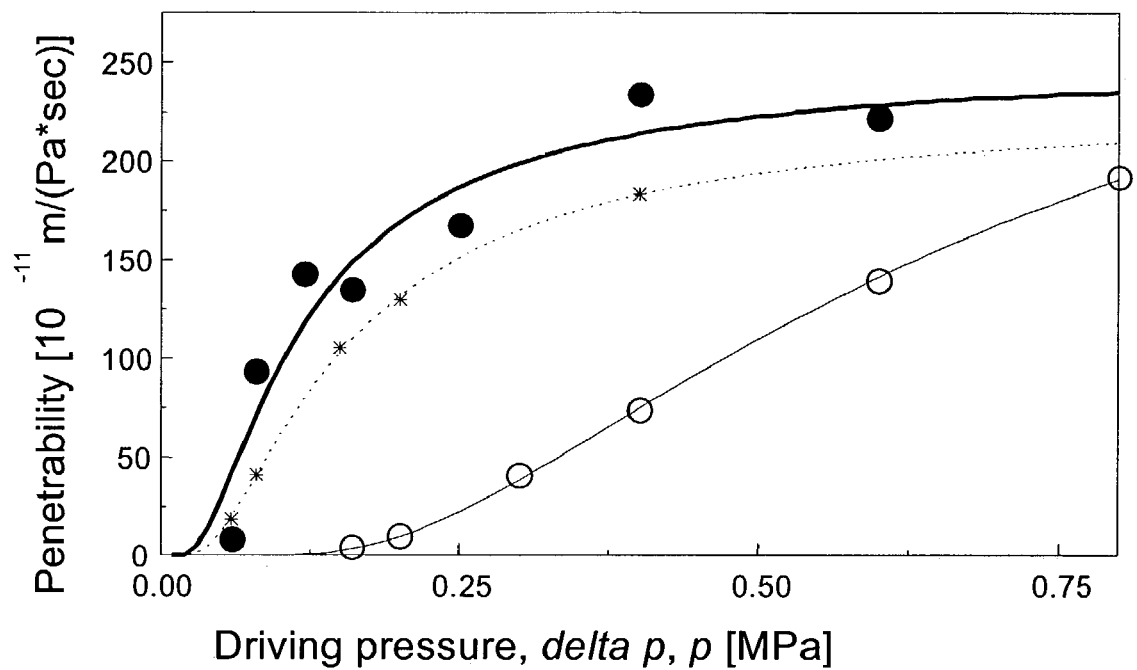
FIG. 2: Penetration curves for SPC/KT 3/1 mole/mole formulation without (o) and with (*)10 rel-mol % of Tween 80. * Reference Tween-Transfersomes®. The curves were calculated as described in FIG. 1, using eq. (*).

Vesicle transport ability (pore penetration capability/ adaptability). Transbarrier flux of the test suspension containing 5 mol-% Tween is much higher than for the formulation that contains merely phospholipid (as the basic amphipat) and ketoprofen (as the surface active, membrane destabilising, surfactant-like amphipat) components. This is clearly seen from FIG. 2, which illustrates pressure dependence of said suspension flux divided by driving pressure.

Examples 8-12

| | Composition of aggregates: |
|---|---|
| 75.0 mg | Phosphatidylcholine from soy-bean (SPC), the actual value is: 75 mg – Tween 80 amount in mg |
| 25.0 mg | Ketoprofen, sodium (KT) |
| see the following table | Tween 80 |
| add 1 ml | Phosphate buffer (pH = 7.2) |

Reference buffer: Phosphate buffer (pH=7.2)

Objective: to study the effect of relative concentration of a surfactant, as the second membrane destabilising amphipat, on adaptability of extended surface mixed amphipat aggregates.

Suspension preparation: as with examples 1-4.

Vesicle transport ability (pore penetration capability/ adaptability) data, as measured in this test series, confirm and expand the findings obtained with examples 1-4. Tween acting as the second membrane destabilising component improves the ability of test suspension to penetrate barriers even when this surfactant is present in the quaternary mixture merely in small amount, as long as relative concentration of Tween is at least approximately 2.5 mol-%, and even better 5 mol-%. Data given in Table 2 justify the conclusion. They are compared with the reference non-ionic Tween-based Transfersome® formulation (Reference Tfs) and with the buffer fluid (Reference fluid) in which mixed amphipat vesicles were suspended.

The suspension viscosity for example 11 was around 730 mPa s at 20 RPM

TABLE 2

Fit results for the pore penetration experiments done with various quaternary suspensions of a phospholipid (SPC; stable membranes forming component), a drug (KT; 1st membrane destabilising component), and Tween 80 (2nd membrane destabilising component) co-suspended in a buffer at different relative concentrations of Tween 80.

| Nr | Tween 80 content [mol % of SPC] | p* [MPa] | $P_{max}$ [$10^{-11}$ m $Pa^{-1}\cdot sec^{-1}$] | Adaptability $a_a$, [$MPa^{-1}$] |
|---|---|---|---|---|
| | 0 | 1.66 ± 0.07 | 345 ± 37 | 0.602 |
| 8 | 1.25 | 0.51 ± 0.05 | 293 ± 23 | 1.961 |
| 9 | 2.5 | 0.50 ± 0.04 | 339 ± 26 | 2.000 |
| 10 | 5 | 0.23 ± 0.03 | 215 ± 19 | 4.348 |
| 11 | 7.5 | 0.22 ± 0.02 | 213 ± 14 | 4.545 |
| 12 | Reference Tfs (Tween) | 0.20 ± 0.01 | 227 ± 3 | 5.000 |
| | Reference fluid (buffer) | Not applicable | 613 ± 15 | Not applicable |

§The quoted error only accounts for analytical and not for experimental data uncertainty, the latter often amounting to 20-30%.
Reference Tfs vesicles were prepared from an equimolar (50/50 mol/mol) SPC/Tween 80 mixture.

Comparative Examples 13-14

| Composition: | |
|---|---|
| 43.65 mg | Phosphatidylcholine from soybean (+95% = PC) |
| 72.00 mg | Tween 80 |
| 34.35 mg | Ketoprofen |
| 6.08 mg | Sodium hydroxide |
| 5.25 mg | Benzyl alcohol |
| 36.51 mg | Ethanol 96% |
| add 1 g | 154 mM phosphate buffer, pH = 7.4 |

Suspension preparation: Formulations were made in accordance with the above compositions.

Hydration of the components mixed in given proportions produced a clear, yellowish fluid. This is indicative of micellar suspension and implies that the tested mixed lipid aggregates are colloidally not stable. Determination of the average diameter of aggregates in such suspension with the dynamic light scattering confirmed the conclusion (mean particle diameter approx. 22 nm, which is incompatible with existence of vesicles).

Diluting the preparation with the corresponding buffer from 15% total lipid to 10% total lipid, making essentially the same observation further corroborated the result. Based on the existing information about phosphatidylcholine solubilisation by Tween 80, even a reduction of relative surfactant concentration by a factor of 2, thus creating a SPC/Tween 80 2/1 mol/mol mixture loaded with approx. 30 mol-% ketoprofen, still would yield unstable aggregates.

Addition of Tween 80 much beyond the rather low relative molar concentration proposed in example 12 thus destabilises the three component lipid aggregates to the point of solubilisation, or at close to this point. Such compositions, therefore, do not fulfil the required stability criterion for the extended surface aggregates required by the present application.

Comparative Examples 15-16

| | Composition: |
|---|---|
| 66.71 mg | Soybean-phosphatidylcholine |
| 11.00 mg | Tween 80 |
| 22.21 mg | Ketoprofen |
| 0.00/66.71 mg | Ethanol (EtOH; for examples 16 and 17, respectively) |
| 11.56 mg | NaOH (30%) |
| 0.50 mg | Na metabisulphite |
| 1.00 mg | Disodium edetate (EDTA) |
| 0.20 mg | Butylhydroxytoluene (BHT) |
| 1.46 mg | Methylparabene |
| 1.00 mg | Linalool |
| 5.25 mg | Benzyl alcohol |
| add 1 g | 7.8 mM Phosphate buffer, pH = 7.2 |

Suspension preparation. Vesicular intermediate preparation with 17.14% total lipid containing no ethanol and ketoprofen in identical concentration as in Example 11 was mixed with the SPC mass equivalent of ethanol. To meet the needs of pharmaceutical formulations as well, several suspension stabilising agents (EDTA, BHA, methylparabene, and benzyl alcohol) were included in the formulation. Characterisation was done as with examples 1-4.

TABLE 3

Results of driving pressure and aggregate adaptability analysis for examples 15 and 16.

| Formulation | p* [MPa] | $P_{max}$ [$10^{-8}$ kg/(m$^2$ · s · Pa)] | Adaptability $a_a$, [MPa$^{-1}$] |
|---|---|---|---|
| Example 15 (no EtOH) | 0.233 ± 0.013[§] | 216.5 ± 7.4 | 4.292 |
| Example 16 (with EtOH) | 0.133 ± 0.006[§] | 254.3 ± 9.7 | 7.519 |

[§]The quoted error only accounts for analytical and not for experimental data uncertainty.

Specifically, the pressure required to drive vesicles through narrow pores, p*, was found to decrease in the presence of EtOH from 0.233 MPa to 0.133 mPa; this is a decrease of approx. 40% and thus near the limit of insignificance (see Table 2 for comparison). The reason is the limited assay resolution, which for p* in the studied situation is 20-30%.

Speaking in absolute terms, and making comparison with the magnitude of positive effect on aggregate adaptability caused by Tween 80 (cf. Tables 2 and 3), ethanol in the ranges tested only increases the adaptability of tested aggregates moderately.

Comparison of the results from experiments 15 and 16 and 11, moreover, confirms that the tested system preservatives (Na metabisulphite; EDTA; BHT, benzyl alcohol) neither affect negatively the desirable extended surface aggregate adaptability nor do they change much the pressure required for driving adequate suspension transport through a nanoporous barrier.

Further, the results, given in Table 3, confirm that the adaptability of the aggregates proposed in the Comparative Examples is far inferior to that of the present formulations.

Examples 19-21

| | Composition: |
|---|---|
| 75 mg | Phosphatidylcholine from soy-bean (SPC), |
| 25 mg | Ketoprofen, sodium (KT) |
| See the following table | Tween 80 (mol-% referring to SPC) |
| add 1 ml | Water or 50 mM buffer (pH = 7.2) |

Objective: to test the influence of ionic strength of the bulk inorganic electrolyte on the adaptability of mixed amphipat aggregates suspended in such an electrolyte.

Suspension preparation and characterisation. The test suspension was prepared essentially as with examples 1-4, except in that the buffer was sometimes exchanged for water with practically the same pH-value. This had important consequences. When the ionic strength (I) of the bulk electrolyte solution with a pH near 7 changes, ketoprofen distribution and degree of ionisation in Transfersome® suspension also changes. This modifies—most probably decreases—extended surface aggregate adaptability, which must be considered when designing products on the basis of given formulation composition. Experimental evidence for this is given in Table 5.

TABLE 5

The fit results based on formula (*) for the transbarrier flux/driving pressure ratio (barrier penetrability), of various quinternary suspensions with KT as the drug in different buffer systems.

| Formulation | p* [MPa] | $P_{max}$ [$10^{-11}$ m Pa$^{-1}$ · sec$^{-1}$] | Adaptability $a_a$, [MPa$^{-1}$] |
|---|---|---|---|
| 10 mol-% Tween no buffer | 0.49 ± 0.02 | 212 ± 8 | 2.041 |
| 10 mol-% Tween, 50 mM buffer, I = 117 mM | 0.25 ± 0.03 | 230 ± 17 | 4.000 |
| 7.5 mol-% Tween, 6.3% v/v EtOH no buffer | 0.31 ± 0.06 | 194 ± 23 | 3.226 |
| 7.5 mol-% Tween, 6.3% v/v EtOH 50 mM buffer, I = 117 mM | 0.13 ± 0.01 | 248 ± 11 | 7.692 |
| Reference Tween Tfs in the buffer | 0.20 ± 0.01 | 227 ± 3 | 5.000 |

Examples 22-23

| | Composition: |
|---|---|
| 75.0 mg | Phosphatidylcholine from soy-bean (SPC), |
| 25 mg | Ketoprofen, sodium (KT) |
| 12.4 mg | Tween 80 |
| add 1 ml | Buffer pH = 7.2 and pH = 7.7 |

Suspension preparation and characterisation: see previous test series.

Objective: to test the effect of ketoprofen ionisation, which above the pKa(KT)~ 6.4 increases with pH, on adaptability of the drug loaded mixed lipid vesicles.

Results: Adaptability of simple formulations containing three amphipatic components was confirmed to depend on the ionisation state of its only titratable component, ketoprofen. Detailed results are given in the following Table 6.

TABLE 6

Fit results, based on eq. (*), for the pressure normalised transbarrier flux of KT-Tfs suspensions at different pH

| pH | $p^*$ [MPa] | $P_{max}$ [$10^{-11}$ m Pa$^{-1}$ · sec$^{-1}$] | Adaptability $a_a$, [MPa$^{-1}$] |
|---|---|---|---|
| 7.2 | 1.66 ± 0.07 | 345 ± 37 | 0.602 |
| 7.7 | 0.62 ± 0.07 | 237 ± 28 | 1.613 |
| Reference Tfs | 0.20 ± 0.01 | 227 ± 2.9 | 5.000 |

Examples 24-25

| | Composition: |
|---|---|
| 100 mg/ml | Phosphatidylcholine from soy-bean (SPC) as large unilamellar vesicle suspension |
| 254 mg/ml | Ketoprofen, sodium (KT) in solution Buffer pH = 7.2 and pH = 7.7 Mixed during experiments to yield increasing relative ratio of KT in SPC aggregates suspension. |

Objective: to test the ability of ketoprofen to solubilise lipid bilayer membranes.

Results: The ability of ketoprofen to solubilise soybean phosphatidylcholine (SPC) membranes was determined by measuring the turbidity of a suspension (10 w-%) of large unilamellar vesicles during successive addition of 1 M solution of ketoprofen. In the first test series this was done in 50 mM phosphate buffer at pH=7.4, where more than 50% of the drug is ionised and more than 50% of the drug is vesicle-bound, but chiefly in the non-charged form, which does not destabilise lipid membranes significantly. SPC vesicles under tested these conditions were not measurably solubilised, despite the presence of some ionised ketoprofen, but were partly destabilised, as demonstrated in previous examples.

The second experiment was performed at pH=11.6, under which condition all ketoprofen molecules are deprotonated and hence have a maximum solubilisation, i.e. membrane destabilisation, capability. Solubilisation of SPC membranes was now observed when the molar ratio for the drug in vesicle bilayers was above ketoprofen/SPC ~10.8/1 mole/mole. SPC-ketoprofen association thus produces weakly bound complexes with membrane solubilising capability.

Examples 26-30

| | Composition: |
|---|---|
| 75.0 mg | Phosphatidylcholine from soy-bean (SPC, used as a saturated ethanolic solution) the actual number is: 75 mg – Brij content |
| 25.0 mg | Ketoprofen, sodium (KT) |
| See the following table | Brij 98 |
| add 1 ml | Phosphate buffer (pH = 7.2) |

Objective: to demonstrate the usefulness of another surfactant, Brij, different from Tween 80, to increase the flux through narrow pores of ketoprofen/SPC extended surface aggregates in a suspension.

Suspension preparation was essentially the same as in examples 1-4.

Flux determination. The flux of suspension of extended surface aggregates containing SPC, KT and, in case, Brij 98 was measured using the same device as is used for aggregate adaptability determination. The only difference was that only a single driving pressure was used for suspension characterisation. For comparison, the ratio of KT-loaded and of empty Brij Transfersomes® was calculated (=Rel. Flux).

The results of the test series measured with Brij 98, a polyoxyethylene-oleyl-ether with 20 OE units in polar head are given in Table 7.

TABLE 7

Flux of mixed amphipat suspensions through 20 nm pores in a semi-permeable barrier driven by trans-barrier pressure of 0.1 MPa.

| Brij 98 content [mol % of SPC] | Flux [mg cm$^{-2}$sec$^{-1}$] | Rel. Flux |
|---|---|---|
| 0 | <1 | |
| 2.5 | 10 | >10 |
| 5.0 | 30 | >30 |
| 7.5 | 29 | >29 |

Examples 31-34

Composition KT Form(ulation) B (Expt 31):

| Weight-% | |
|---|---|
| 2.857 | Ketoprofen (USP) |
| 7.143 | Phosphatidylcholine |
| 3.000 | Glycerol (USP) |
| 2.087 | Sodium Hydroxide, 50% (FCC) |
| 0.120 | Phosphate buffer salts |
| 0.100 | Linalool |
| 0.100 | Disodium edetate EDTA |
| 1.250 | Carbomer 974 |
| 0.100 | Carbomer 1342 |
| 1.000 | Propylen Glycol |
| 0.200 | Ethylparaben |
| 0.525 | Benzyl Alcohol |
| 0.020 | Butylated hydroxytoluene |
| 81.499 | Water |

Composition KT Form.(ulation) A (Expt 32):

| Weight-% | |
|---|---|
| 2.290 | Ketoprofen |
| 6.870 | Soy Phosphatidylcholine (SPC) |
| 0.850 | Polysorbate (Tween 80) |
| 3.651 | Ethanol 96% |
| 0.930 | NaOH (sodium hydroxide) |
| 0.235 | Phosphate buffer salts |
| 0.050 | Sodium metabisulphite |
| 0.020 | Butylhydroxytoluene (BHT) |
| 0.100 | Disodium edetate (EDTA) |
| 0.250 | Methyl parahydroxybenzoate |
| 0.525 | Benzyl alcohol |
| 0.100 | Linalool |
| 1.250 | Carbomer (Carbopol 980) |
| 3.00 | Glycerol |
| 79.879 | Water |

Commercial topical formulation Gabrilen (Expt. 33): according to desk physicians' reference, the preparation contains 25 mg KT/g gel, supplemented with 96% ethanol, 3-propanol, 10% ammonia solution and Carbomer in purified water.

Commercial oral formulation Ketoprofen Ratiopharm (KT Ratiopharm) (Expt. 34): according to desk physicians' reference each film tablet contains 50 mg KT in addition to microcrystalline cellulose, gelatine, SiO2, corn starch, talcum, crosscarmelose sodium, Mg stearate, hypromelose, macrogol, glycerol, dyes E 171 and E 172.

Preparation of formulations A and B, which both contained extended surface vesicles, was done essentially as described for examples 1-4. Commercial comparators were purchased in a local pharmacy and used as obtained.

Methodology: The test pigs were numbered and central vein catheters were implanted into the animals. The application area on a hind limb of each animal was shaved with an electric clipper and cleaned with warm water and soap. Then, an application area of 10 cm×10 cm (=100 cm$^2$) was marked.

At time zero of the sampling period, 2 ml of the blood were sampled from each test animal into a citrate-coated vial to generate plasma. The pigs were anaesthetised for approximately 60 min and the appropriate dose of the test medication was applied onto the application site of a pig or else was given to the animal orally. Further plasma samples (0.5 ml each) were taken 0.5, 1, 2, 3, 5, 8 and 12 hours post application. They were kept frozen until analysis.

Ketoprofen concentration was determined with HPLC using standard methods, in case of muscle tissue samples after the specimen homogenisation. Area under the curve (AUC) was calculated by integrating all time-point data.

Figure 3:
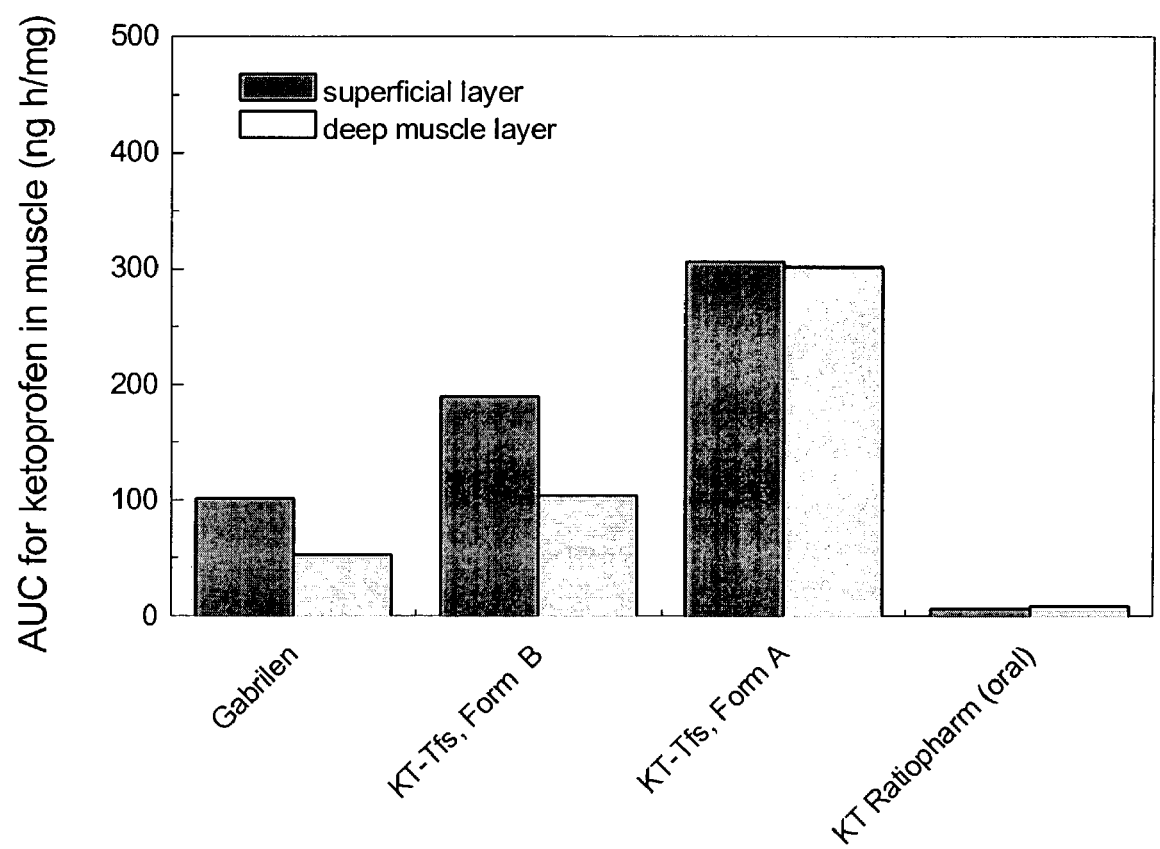
FIG. 3: Area under the curve (AUC), which reflects the cumulative delivery of the drug, calculated from the pharmacokinetic results measured with different ketoprofen (KT) formulations tested in pigs (n=4).

Results of experiments are given in Tables 8 and FIG. 3. Whereas the individual pharmacokinetic data sets are rather scattery, yielding standard deviations comparable to the mean because of small group size, the overall data analysis does demonstrate the superiority of at least three amphipat component preparations, in comparison with two amphipat component formulations, to deliver an NSAID (ketoprofen) deep under the application site on the skin. The greater is the investigated tissue depth the greater is the observed advantage (superficial muscle=0-1.5 cm; deep muscle>1.5 cm).

TABLE 8a

Area under the curve (AUC$_{0-8h}$ [ng × mg$^{-1}$ × h]), measured with different KT formulations in pigs

|  | Gabrilen ® (n = 4) | Formulation B (n = 7) | Formulation A (n = 7) | KT Ratiopharm ® (oral, n = 3) |
|---|---|---|---|---|
| Superficial muscle tissue | 102 | 209 | 306 | 7 |
| Deep muscle tissue | 53 | 147 | 301 | 9 |

TABLE 8b

Ketoprofen (KT) concentration in superficial muscle tissue (ng/mg)

| Time (hours) | Gabrilen ® (n = 4) | KT-Tfs Form. B (n = 7) | KT-Tfs Form. A (n = 7) | KT-Ratiopharm (oral) (n = 3) |
|---|---|---|---|---|
| 0 | 0.0 ± 0.0 | 0.0 ± 0.0 | 0.0 ± 0.1 | 0.0 ± 0.0 |
| 1 | 5.0 ± 3.3 | 50.4 ± 48.6 | 55.5 ± 66.3 | 1.0 ± 1.2 |
| 2 | 12.8 ± 22.6 | 75.2 ± 83.8 | 36.3 ± 32.1 | 1.6 ± 1.2 |
| 3 | 10.9 ± 11.5 | 3.0 ± 3.2 | 25.7 ± 28.5 | 1.4 ± 0.3 |
| 5 | 19.3 ± 18.7 | 12.9 ± 11.1 | 45.2 ± 72.9 | 0.7 ± 0.2 |
| 8 | 3.8 ± 3.8 | 19.6 ± 17.9 | 22.0 ± 17.9 | 0.2 ± 0.1 |

TABLE 8c

Ketoprofen (KT) concentration in deep muscle tissue (ng/mg)

| Time (hours) | Gabrilen ® (n = 4) | KT-Tfs Form. B (n = 7) | KT-Tfs Form. A (n = 7) | KT-Ratiopharm (oral) (n = 3) |
|---|---|---|---|---|
| 0 | 0.0 ± 0.0 | 0.0 ± 0.0 | 0.0 ± 0.1 | 0.0 ± 0.0 |
| 1 | 2.6 ± 2.3 | 53.4 ± 66.5 | 24.8 ± 19.0 | 1.5 ± 1.6 |
| 2 | 5.4 ± 9.3 | 63.0 ± 51.9 | 18.8 ± 21.5 | 1.8 ± 1.0 |
| 3 | 9.0 ± 9.3 | 1.4 ± 0.8 | 49.8 ± 71.8 | 1.6 ± 0.5 |
| 5 | 7.9 ± 5.8 | 5.6 ± 2.2 | 49.9 ± 65.0 | 1.0 ± 0.2 |
| 8 | 2.9 ± 2.9 | 14.1 ± 10.9 | 30.2 ± 28.7 | 0.3 ± 0.2 |

Examples 35-36

Composition for ketoprofen in carrier suspension (KT-Tfs sol):

| Weight-% | |
|---|---|
| 3.435 | Ketoprofen (KT) |
| 10.305 | Soy Phosphatidylcholine (SPC) |
| 1.275 | Polysorbate (Tween 80) |
| 5.477 | Ethanol 96% |
| 0.533 | NaOH (sodium hydroxide) |
| 0.235 | Phosphate buffer salts |
| 0.050 | Sodium metabisulphite |
| 0.020 | Butylhydroxytoluene (BHT) |
| 0.100 | Disodium edetate (EDTA) |
| 0.250 | Methyl parahydroxybenzoate |
| 0.525 | Benzyl alcohol |
| 0.100 | Linalool |
| 3.00 | Glycerol |
| 74.695 | Water |

Composition for ketoprofen in carrier gel (KT-Tfs gel):

As in experiment 35, except in that the first four components are diluted 1.5-fold and Carbomer (Carbopol 980), buffered to pH=7.2, is included to final concentration of 1.25 w-%.

Objective: to test the effect of formulation viscosity, and the presence of a thickening agent as viscosity modifier, on the ability of NSAID loaded extended surface aggregates to deliver the drug (ketoprofen) deep under the application site on the skin.

Methodology was the same as in experiments 31-34, except in that no oral comparator was included. A total of 4 pigs were used in each group.

Area under the curve (AUC) was calculated by integrating all PK (pharmacokinetic) data measured in different tissues (plasma, not shown) and the muscles under drug application site on the skin. The results obtained for superficial (0-1.5 cm) and deep (>1.5 cm) muscle are given in Tables 9, and suggest no detrimental effect of the thickening agents used in KT-Tfs gel to achieve the desired suspension viscosity of approx. 730 mPa s. If anything, the thickening agent present in the tested gel is beneficial.

TABLE 9a

Area under the curve ($AUC_{0-8h}$ [ng × $mg^{-1}$ × h]),
measured with two carrier-based ketoprofen (KT) formulations in pigs

|  | KT-Tfs gel 17 mg (n = 4) | KT-Tfs sol. 17 mg (n = 4) | KT-Tfs gel 50 mg (n = 4) | KT-Tfs sol. 50 mg (n = 4) |
|---|---|---|---|---|
| Superficial muscle tissue | 147 | 44 | 278 | 186 |
| Deep muscle tissue | 97 | 63 | 266 | 202 |

TABLE 9b

KT concentration in superficial muscle tissue (ng/mg)

| Time (hours) | KT-Tfs gel 17 mg (n = 4) | KT-Tfs sol. 17 mg (n = 4) | KT-Tfs gel 50 mg (n = 4) | KT-Tfs sol. 50 mg (n = 4) |
|---|---|---|---|---|
| 0 | 0.0 ± 0.0 | 0.0 ± 0.0 | 0.0 ± 0.1 | 0.0 ± 0.0 |
| 1 | 83.3 ± 82.9 | 2.3 ± 1.5 | 55.5 ± 66.3 | 23.0 ± 29.3 |
| 2 | 24.1 ± 27.5 | 0.8 ± 0.3 | 36.3 ± 32.1 | 21.2 ± 33.6 |
| 3 | 8.1 ± 8.0 | 2.8 ± 0.1 | 25.7 ± 28.5 | 9.0 ± 2.1 |
| 5 | 14.2 ± 14.2 | 10.6 ± 12.5 | 45.2 ± 72.9 | 34.8 ± 49.8 |
| 8 | 3.1 ± 2.6 | 3.5 ± 2.4 | 22.0 ± 17.9 | 29.8 ± 50.1 |

TABLE 9c

KT concentration in deep muscle tissue (ng/mg)

| Time (hours) | KT-Tfs gel 17 mg (n = 4) | KT-Tfs sol. 17 mg (n = 4) | KT-Tfs gel 50 mg (n = 4) | KT-Tfs sol. 50 mg (n = 4) |
|---|---|---|---|---|
| 0 | 0.0 ± 0.0 | 0.0 ± 0.0 | 0.0 ± 0.1 | 0.0 ± 0.0 |
| 1 | 36.0 ± 49.1 | 14.1 ± 1.5 | 24.8 ± 19.0 | 24.5 ± 44.7 |
| 2 | 19.4 ± 23.5 | 0.8 ± 0.3 | 18.8 ± 21.5 | 4.5 ± 4.0 |
| 3 | 2.4 ± 2.6 | 9.2 ± 3.1 | 49.8 ± 71.8 | 25.4 ± 43.0 |
| 5 | 13.5 ± 8.8 | 9.3 ± 12.5 | 49.9 ± 65.0 | 46.6 ± 85.6 |
| 8 | 2.4 ± 1.4 | 6.4 ± 2.4 | 30.2 ± 28.7 | 15.6 ± 23.4 |

The invention claimed is:

1. A vesicular composition comprising:
   1) vesicles having a lipid bilayer and consisting essentially of:
      i) a phosphatidylcholine;
      ii) a polyethyleneglycol-sorbitan-monooleate, a polyoxyethylene-oleoyl ether, or a nonaethyleneglycoloctylphenyl ether surfactant; and
      iii) a salt of an NSAID wherein said NSAID is diclofenac, ibuprofen or ketoprofen; and
   2) a pharmaceutically acceptable, polar liquid medium, wherein
   the phosphatidylcholine and the surfactant of the vesicles are present in a molar ratio of between about 20/1 and about 7.5/1,
   the molar ratio of phosphatidylcholine to NSAID is between about 10/1 to about 1/1,
   the lipid bilayer is in the fluid lamellar phase, and
   the pH of the composition is above the pKa of the NSAID.

2. The composition of claim 1, wherein the phosphatidylcholine is from soy bean, coconut, olive, safflower, or sunflower, linseed, evening primrose, primrose, or castor oil.

3. The composition of claim 1, wherein the total dry mass of the phosphatidylcholine, the surfactant, and the NSAID is between 0.01 weight-% and 50 weight-% of the composition.

4. The composition of claim 1, further comprising a lower aliphatic alcohol.

5. The composition of claim 4, wherein the alcohol is n-propanol, isopropanol, 2-propanol, n-butanol, 2-butanol, 1,2-propanediol, 1,2-butanediol, or ethanol.

6. The composition of claim 1, wherein the pH of the composition is between 6.4 and 8.3.

7. The composition of claim 1, wherein the ionic strength of the composition is between 0.005 and 0.3.

8. The composition of claim 1, wherein the viscosity of the composition is between 50 mPas and 30,000 mPas.

9. A method for treating peripheral pain or inflammation comprising applying the composition of claim 1 to the skin of a warm blooded mammal.

10. A non-occlusive patch comprising the composition of claim 1.

11. The composition of claim 1, wherein the total dry mass of, the polyethyleneglycol-sorbitan-monooleate, polyoxyethylene-oleoyl ether, or nonaethyleneglycol octylphenyl ether surfactant; and the NSAID is between 0.01 weight-% and 50 weight-%.

12. The composition of claim 1, wherein the phosphatidylcholine is soy phosphatidylcholine or egg lecithin.

13. The composition of claim 1 wherein the salt of the NSAID is the sodium salt of ketoprofen.

14. The composition of claim 1, wherein the phosphatidylcholine is soy phosphatidylcholine, the surfactant is polyethyleneglycol-sorbitan-monooleate, and the salt of the NSAID is the sodium salt of ketoprofen.

15. The composition of claim 1, wherein the molar ratio of phosphatidylcholine to NSAID is between about 3/1 to about 1/1.

16. The composition of claim 15, wherein the molar ratio of phosphatidylcholine to NSAID is between about 2.5/1 to about 1/1.

17. The composition of claim 16, wherein the molar ratio of phosphatidylcholine to NSAID is between about 2/1 to about 1/1.

18. The composition of claim 17, wherein the molar ratio of phosphatidylcholine to NSAID is about 1/1.

19. The composition of claim 14, wherein the molar ratio of phosphatidylcholine to NSAID is between about 3/1 to about 1/1.

20. The composition of claim 19, wherein the molar ratio of phosphatidylcholine to NSAID is between about 2.5/1 to about 1/1.

21. The composition of claim 20, wherein the molar ratio of phosphatidylcholine to NSAID is between about 2/1 to about 1/1.

22. The composition of claim 21, wherein the molar ratio of phosphatidylcholine to NSAID is about 1/1.

23. The method of claim 9, wherein the molar ratio of phosphatidylcholine to NSAID is between about 3/1 to about 1/1.

24. The method of claim 23, wherein the molar ratio of phosphatidylcholine to NSAID is between about 2.5/1 to about 1/1.

25. The method of claim 24, wherein the molar ratio of phosphatidylcholine to NSAID is between about 2/1 to about 1/1.

26. The method of claim 25, wherein the molar ratio of phosphatidylcholine to NSAID is about 1/1.

27. A method for treating peripheral pain or inflammation comprising applying the patch of claim 1, to the skin of a warm blooded mammal.

28. The method of claim 27, wherein the molar ratio of phosphatidylcholine to NSAID is between about 3/1 to about 1/1.

29. The method of claim 28, wherein the molar ratio of phosphatidylcholine to NSAID is between about 2.5/1 to about 1/1.

30. The method of claim 29, wherein the molar ratio of phosphatidylcholine to NSAID is between about 2/1 to about 1/1.

31. The method of claim 30, wherein the molar ratio of phosphatidylcholine to NSAID is about 1/1.

32. The composition of claim 1, wherein the pH of the composition is between 0.2 and 2.2 pH units above the pKa of the NSAID.

33. The composition of claim 32, wherein the pH of the composition is between 0.5 and 1.9 pH units above the pKa of the NSAID.

34. The composition of claim 33, wherein the pH of the composition is between 0.8 and 1.6 pH units above the pKa of the NSAID.

35. The composition of claim 1, wherein the phosphatidylcholine is from egg or soya beans.

36. The composition of claim 1, further comprising a thickening agent; an antioxidant, or a microbicide.

37. The composition of claim 1, wherein the phosphatidylcholine and the surfactant are present in a molar ratio of between about 14/1 and about 10/1.

38. The composition of claim 1, wherein the pH is between 0.2 and 2.2 pH units above the pKa of the NSAID.

39. A method for treating peripheral pain or inflammation comprising applying the composition of claim 38, to the skin of a warm blooded mammal.

40. The method of claim 39, wherein the pH is between 0.2 and 2.2 pH units above the pKa of the NSAID.

41. A vesicular composition comprising:
1) vesicles consisting essentially of:
   i) a phosphatidylcholine;
   ii) a polyethyleneglycol-sorbitan-monooleate, a polyoxyethylene-oleoyl ether, or a nonaethyleneglycoloctylphenyl ether surfactant; and
   iii) a salt of an NSAID wherein said NSAID is diclofenac, ibuprofen or ketoprofen; and
2) a pharmaceutically acceptable, polar liquid medium, wherein
   the phosphatidylcholine and the surfactant of the vesicles are present in a molar ratio of between about 20/1 and about 7.5/1,
   the molar ratio of phosphatidylcholine to NSAID is between about 10/1 to about 1/1,
   the vesicles are capable of penetrating a barrier with pores having an average pore diameter at least 50% smaller than the average vesicle diameter before the penetration, and
   the pH of the composition is above the pKa of the NSAID.

42. The composition of claim 41, wherein the phosphatidylcholine is from soy bean, coconut, olive, safflower, or sunflower, linseed, evening primrose, primrose, or castor oil.

43. The composition of claim 41 wherein the total dry mass of the phosphatidylcholine, the surfactant, and the NSAID is between 0.01 weight-% and 50 weight-% of the composition.

44. The composition of claim 41, further comprising a tower aliphatic alcohol.

45. The composition of claim 44, wherein the alcohol is n-propanol, isopropanol, 2-propanol, n-butanol, 2-butanol, 1,2-propanediol, 1,2-butanediol, or ethanol.

46. The composition of claim 41, wherein the pH of the composition is between 6.4 and 8.3.

47. The composition of claim 41, wherein the ionic strength of the composition is between 0.005 and 0.3.

48. The composition of claim 41, wherein the viscosity of the composition is between 50 mPa s and 30,000 mPa s.

49. The composition of claim 41, wherein the total dry mass of, the phosphatidylcholine; the polyethyleneglycol-sorbitan-monooleate, polyoxyethylene-oleoyl ether, or nonaethyleneglycol octylphenyl ether surfactant; and the NSAID is between 0.01 weight-% and 50 weight-%.

50. The composition of claim 41, wherein the phosphatidylcholine is soy phosphatidylcholine or egg lecithin.

51. The composition of claim 41 wherein the salt of the NSAID is the sodium salt of ketoprofen.

52. The composition of claim 41, wherein the molar ratio of phosphatidylcholine to NSATD is between about 3/1 to about 1/1.

53. The composition of claim 52, wherein the molar ratio of phosphatidylcholine to NSAID is between about 2.5/1 to about 1/1.

54. The composition of claim 53, wherein the molar ratio of phosphatidylcholine to NSAID is between about 2/1 to about 1/1.

55. The composition of claim 54, wherein the molar ratio of phosphatidylcholine to NSAID is about 1/1.

56. The composition of claim 41, wherein the phosphatidylcholine is soy phosphatidylcholine, the surfactant is polyethyleneglycol-sorbitan-monooleate, and the salt of the NSAID is the sodium salt of ketoprofen.

57. The composition of claim 56, wherein the molar ratio of phosphatidylcholine to NSAID is between about 3/1 to about 1/1.

58. The composition of claim 57, wherein the molar ratio of phosphatidylcholine to NSAID is between about 2.5/1 to about 1/1.

59. The composition of claim 58, wherein the molar ratio of phosphatidylcholine to NSAID is between about 2/1 to about 1/1.

60. The composition of claim 59, wherein the molar ratio of phosphatidylcholine to NSAID is about 1/1.

61. The composition of claim 41, wherein the pH of the composition is between 0.2 and 2.2 pH units above the pKa of the NSAID.

62. The composition of claim 61, wherein the pH of the composition is between 0.5 and 1.9 pH units above the pKa of the NSAID.

63. The composition of claim 62, wherein the pH of the composition is between 0.8 and 1.6 pH units above the pKa of the NSAID.

64. The composition of claim 41, wherein the phosphatidylcholine is from egg or soya beans.

65. The composition of claim 41, further comprising a thickening agent, an antioxidant, or a microbicide.

66. The composition of claim 41, wherein the phosphatidylcholine and the surfactant are present in a molar ratio of between about 14/1 and about 10/1.

67. The composition of claim 66, wherein the pH is between 0.2 and 2.2 pH units above the pKa of the NSAID.

68. A method for treating peripheral pain or inflammation comprising applying the composition of claim 41 to the skin of a warm blooded mammal.

69. The method of claim 68, wherein the molar ratio of phosphatidylcholine to NSAID is between about 3/1 to about 1/1.

70. The method of claim 69, wherein the molar ratio of phosphatidylcholine to NSAID is between about 2.5/1 to about 1/1.

71. The method of claim 70, wherein the molar ratio of phosphatidylcholine to NSAID is between about 2/1 to about 1/1.

72. The method of claim 71, wherein the molar ratio of phosphatidylcholine to NSAID is about 1/1.

73. A method for treating peripheral pain or inflammation comprising applying the composition of claim 66 to the skin of a warm blooded mammal.

74. The method of claim 73, wherein the pH is between 0.2 and 2.2 pH units above the pKa of the NSAID.

75. A non-occlusive patch comprising the composition of claim 41.

76. A method for treating peripheral pain or inflammation comprising applying the patch of claim 75 to the skin of a warm blooded mammal.

77. The method of claim 76, wherein the molar ratio of phosphatidylcholine to NSAID is between about 3/1 to about 1/1.

78. The method of claim 77, wherein the molar ratio of phosphatidylcholine to NSAID is between about 2.5/1 to about 1/1.

79. The method of claim 78, wherein the molar ratio of phosphatidylcholine to NSAID is between about 2/1 to about 1/1.

80. The method of claim 79, wherein the molar ratio of phosphatidylcholine to NSAID is about 1/1.

* * * * *

UNITED STATES PATENT AND TRADEMARK OFFICE
CERTIFICATE OF CORRECTION

PATENT NO.        : 7,473,432 B2
APPLICATION NO.   : 10/357617
DATED             : January 6, 2009
INVENTOR(S)       : Gregor Cevc and Ulrich Vierl It is certified that error appears in the above-identified patent and that said Letters Patent is hereby corrected as shown below:

On the Title page of the patent, at number (73), replace "Idea AG" with "IDEA AG".

At column 30, line 66, replace "claim 1" with "claim 10".

At column 31, line 64, replace "tower" with "lower".

At column 32, line 17, replace "NSATD" with "NSAID".

Signed and Sealed this

Tenth Day of February, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,473,432 B2
APPLICATION NO. : 10/357617
DATED : January 6, 2009
INVENTOR(S) : Cevc et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (553) days Delete the phrase "by 553 days" and insert -- by 526 days --

Signed and Sealed this

Twenty-fourth Day of November, 2009

David J. Kappos
*Director of the United States Patent and Trademark Office*